(12) United States Patent
Stasiak et al.

(10) Patent No.: US 7,597,814 B2
(45) Date of Patent: Oct. 6, 2009

(54) STRUCTURE FORMED WITH TEMPLATE HAVING NANOSCALE FEATURES

(75) Inventors: James W. Stasiak, Lebanon, OR (US); Kevin Francis Peters, Corvallis, OR (US); Pavel Kornilovich, Corvallis, OR (US)

(73) Assignee: Hewlett Packard Development Company, L.P., Houston, TX (US)

( * ) Notice: Subject to any disclaimer, the term of this patent is extended or adjusted under 35 U.S.C. 154(b) by 1065 days.

(21) Appl. No.: 10/807,873

(22) Filed: Mar. 23, 2004

(65) Prior Publication Data

US 2005/0214661 A1 Sep. 29, 2005

(51) Int. Cl.
*C03C 25/26* (2006.01)
(52) U.S. Cl. .............................. 216/39; 216/40; 216/48; 216/54
(58) Field of Classification Search ................... 216/39, 216/40, 48, 54
See application file for complete search history.

(56) References Cited

U.S. PATENT DOCUMENTS

| 5,776,748 | A | 7/1998 | Singhvi |
| 5,948,621 | A | 9/1999 | Turner et al. |
| 6,828,244 | B2 * | 12/2004 | Chou ........................ 438/706 |
| 2002/0119251 | A1 | 8/2002 | Chen et al. |
| 2003/0032046 | A1 | 2/2003 | Duffy et al. |
| 2003/0054342 | A1 | 3/2003 | Star et al. |
| 2004/0038556 | A1 * | 2/2004 | French et al. ............... 438/800 |
| 2004/0071924 | A1 * | 4/2004 | Yang et al. ................. 428/65.3 |
| 2005/0118338 | A1 | 6/2005 | Steve et al. |
| 2006/0237881 | A1 * | 10/2006 | Guo et al. .................... 264/496 |

FOREIGN PATENT DOCUMENTS

| EP | 1 484 644 A | 12/2004 |
| WO | 2004/092836 A | 10/2004 |

OTHER PUBLICATIONS

Chou, S. et al "Imprint Lithography with Sub-10 nm Feature Size and High Throughput", Microelectronic Engineering, V. 35(1), Feb. 1997. pp. 237-240.
Pfeiffer K et al, "Polymer stamps for nanoimpringing", Microelectronic Engineering, V 61-62, Jul. 2002, pp. 393-398.
Schift H et al, "Chemical non-patterning using hot embossing lithography", Microelectronic Engineering, V. 61-62, Jul. 2002, pp. 423-428.
Elsner C et al, "3D-microstructure replication processes using UV-curable acrylates", Microelectronic Engineering, V 65 (1-2, pp. 163-170, 2003).

* cited by examiner

*Primary Examiner*—Binh X Tran

(57) ABSTRACT

A structure is provided that is formed with a template defining a pattern having nanoscale features. The template may be positioned on a substrate and include a resist layer having openings formed therein, where the template is configured to accommodate the controlled assembly of nanoscale objects.

14 Claims, 19 Drawing Sheets

STRUCTURE FORMED WITH TEMPLATE HAVING NANOSCALE FEATURES

BACKGROUND

One primary motivation of circuit designers of silicon integrated circuits is to reduce the size of the chip space required for circuit components. Reducing the utilized chip space reduces the amount of power required to operate the chip, reduces the temperature of the circuit, and allows the circuit to operate faster. Some solutions have been proposed to create silicon integrated circuits on the nanometer scale ($1 \times 10^{-9}$ meters), or nanoscale, but each has limitations.

Much research is being dedicated to study nanoscale objects, and attempts have been made to build nanoscale objects in a controlled manner. Proposed solutions include the use of anodized aluminum templates, oriented block copolymers, self-assembled diblock copolymers, and patterning with packed layers of nanoscale objects. These approaches have significant limitations.

Nanoscale objects have been created with anodized aluminum templates. In this process, an aluminum layer is anodized to create openings through the layer. The openings in the anodized aluminum are used in an attempt to establish a grid of holes. These holes protrude down through the aluminum template to a substrate below. However, since the anodizing of the aluminum creates unpredictable patterns of openings in the aluminum layer, there is little control with respect to where the openings and the corresponding holes are located. There is little control over the size, shape, or arrangement of the openings.

Another approach to creating nanoscale objects utilizes diblock copolymers. With diblock copolymers, the order of a pattern of openings is controlled by nature. This approach does not provide regular patterns or spatially symmetric opening arrangements. There is no correlation with respect to distances and orientations, making placement of nanoscale objects random and difficult to incorporate into engineered structures that require a higher degree of order. Similar problems exist when using self-assembled copolymers. Templates fabricated using diblock copolymer or self-assembled copolymer approaches do not provide regular patterns or spatially symmetric opening arrangements.

Another approach is the microsphere method, where a substrate's surface is populated with nanoscale objects. When packing is achieved, the objects abut against each other, forming spaces where the objects abut to provide inclusions. The shape and size of the openings are determined by the spaces that are formed at the interstices where the objects contact. Thus, the range of opening geometries that can be generated is limited, and there is no control over the pattern's orientation.

None of the available methods provides the ability to create nanoscale structures on a substrate where the number, size, shape, pattern, orientation, and position of the structures can be controlled. Therefore, there exists a need for a method and system that can create nanoscale structures on a substrate where the number, size, shape, pattern, orientation, and position of the nanoscale structures can be controlled. If this could be done, structures, devices, and circuits could be manufactured on the nanoscale, and chip space could be reduced. As discussed below, embodiments of the invention accomplishes this in a unique and elegant manner.

DETAILED DESCRIPTION

One embodiment of the invention, for example, is directed to nanoscale structures created with methods by which the number, size, shape, orientation, pattern, and position of the nanoscale objects are controlled. Desired nanoscale objects can be made proximal to a substrate surface using a template to aid in placing and orienting nanoscale objects. Objects may be controllably placed in desired locations, in a periodic or non-periodic manner, or in predetermined patterns. These structures may be used to create circuit components and other structures to produce a device or an electronic circuit on a substrate. It will be appreciated by those skilled in the art, however, that other embodiments of the invention may be implemented in applications where nanoscale features are useful, without departing from the spirit and scope of the invention, which is defined in the appended claims and their equivalents.

In one embodiment a method is used to form a structure with a template defining a pattern having nanoscale features positioned on or about a substrate. The template is formed from a resist layer having openings and is configured to accommodate the controlled assembly of nanoscale objects by aiding in the positioning of nanoscale objects about the template and proximal to a substrate surface. The result is a structure having nanoscale features in predetermined numbers, size, shape, orientation, pattern, and/or position.

Figure 1:
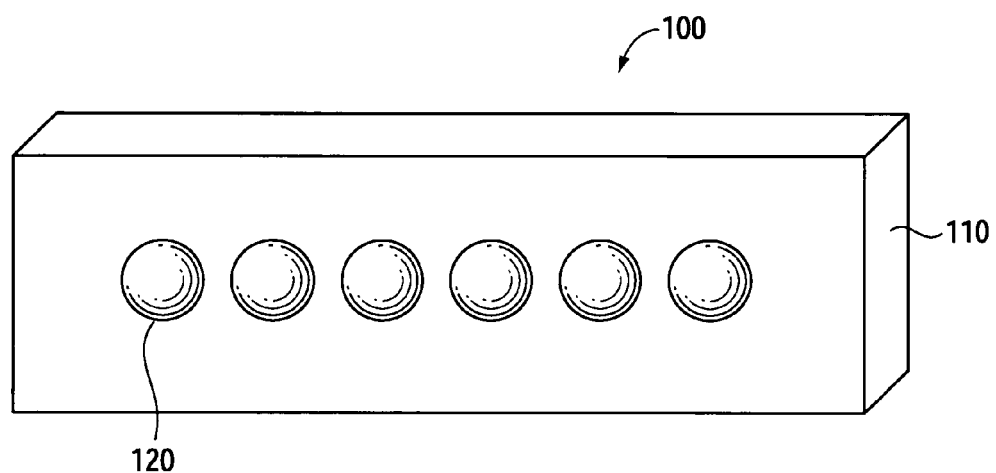
FIG. 1 is an illustration of a structure, in accordance with one embodiment of the invention.

Referring to FIG. 1, one such structure 100 is illustrated having nanoscale objects 120 attached to a substrate 110. The number, size, shape, pattern, orientation, and position of the nanoscale objects 120 on the substrate 110 may be controlled using a template (shown below) having openings corresponding to the nanoscale objects.

One method of creating the template utilizes a patterned mold. One method of creating the mold is by using an electron beam or other apparatus or process to add or remove material from a wafer, leaving a mold having predictable nanoscale features corresponding to a predetermined pattern.

The pattern created in the mold is used to stamp out a template on a surface of a wafer structure, for example. The wafer structure may include a layer of resist above a substrate, or other material that is able to accommodate a template pattern. The mold is then removed, leaving the template pattern in the resist layer on or about the substrate. Residual resist material on the substrate that deviates from the desired template pattern may be removed with a chemical wash or other process. Thus, the patterned resist layer forms a template having a nanoscale pattern that is complementary to the mold. The template has openings or other structures for accommodating nanoscale objects, and is used as a guide for depositing the objects into the openings to position and orient them about or proximal to the substrate's surface. The template may be configured to accommodate the growth of nanoscale objects through the openings. Nanoscale objects may be placed on the substrate at locations and orientations dictated by the template design. Nanoscale patterns can then be created having predetermined positions, orientations, and patterns that may be non-periodic, as well as periodic. Once the nanoscale objects have been placed into the openings of the template, the template may then be removed. The template is configured to be removed from the substrate without removing the nanoscale objects. Alternatively, the template may remain on the substrate.

FIGS. 2-12 illustrate an example of how a mold, a corresponding template and a resulting structure may be created according to the invention. The example shown illustrates a simplified embodiment of the invention in terms of both method and structure. Other embodiments are contemplated to be within the scope of the invention as defined by the appended claims.

Figure 2:
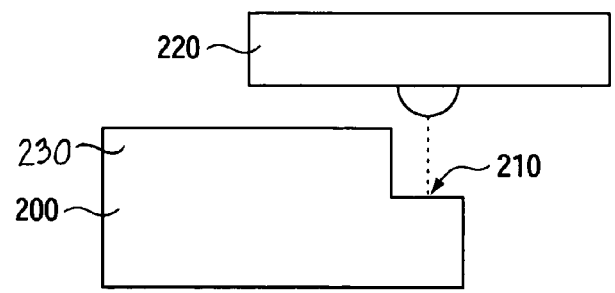
FIG. 2 is an illustration of a wafer being created, in accordance with one embodiment to the invention.

Referring to FIG. 2, a wafer 200 is shown used in the creation of a patterned mold having nanoscale features. In one embodiment, the mold is created on the wafer 200 according to a pattern that is made using e-beam lithography where an electron beam 220 is used to carve a mold from an appropriate resist layer 230. The mold is created using a resist layer. The space 210 represents a first open area of the mold pattern. The pattern created in the mold by the electron beam is a pattern of nanoscale features in the form of openings and structures. In one embodiment, the mold pattern is an ordered pattern of nanoscale features. It is noted that the mold could also be created by alternative means such as focused ion beam (FIB) or extreme ultraviolet (EUV) techniques.

According to an embodiment of the invention, the mold is used to fabricate a "template" from a resist material that covers, or partially covers, a substrate surface. Utilizing a process known in the art as "thermal imprint lithography", for example, the mold is stamped into the resist material at an elevated temperature and elevated pressure. The mold is then removed and the resist is set upon cooling. In yet another embodiment, the mold is stamped into the resist and the resist is set by ultra-violet curing by a process known in the art as a "step and flash" lithographic method.

The mold may be fashioned in a shape complementary to the desired template pattern. In one embodiment, for example, the mold is created by carving a wafer in an inverse or complementary pattern. The desired template pattern has nanoscale features created in a template layer on the substrate surface. The material of the wafer could be any suitable material that will be rigid enough to stamp out the pattern in the material of the template. For example, the mold could be made from metal, silicon, silicon dioxide, plastic, glass, or quartz, and the template may be made from a more malleable material such as materials commonly used as photoresist on substrates. Examples might include Polymethyl Methacrylate (PMMA) and resin-based resists such as those made by Clariant Corporation's AZ Electronic Materials™ and Shipley Novlak™.

There are many possible methods of "imprinting", though the invention is not limited to any particular methods. In one embodiment, thermal imprint relies on pressing the mold into a "resist" layer at high temperatures and high pressure. For this application, there is no requirement for the resist to be photosensitive and resist layers of PMMA, etc. are appropriate. Another approach, "step-and-flash" lithography, does require a photosensitive resist layer. In this approach, a transparent mold (quartz for example) is pressed into the resist layer while shining light at the appropriate wavelength and intensity through the mold. Like traditional photolithography, the exposed resist is crosslinked and becomes insoluble in the developer chemistry. The advantage of the step-and-flash (SFIL) approach is reduced imprint pressure and substantially lower temperatures, which makes it possible to repeat the imprint process and build up vertical structures. The resists for step-and-flash are typically low viscosity photoploymerizable, organosilicon solutions. Molecular Imprints sells a resist called MonoMat™ that works well for most applications.

Figure 3A:
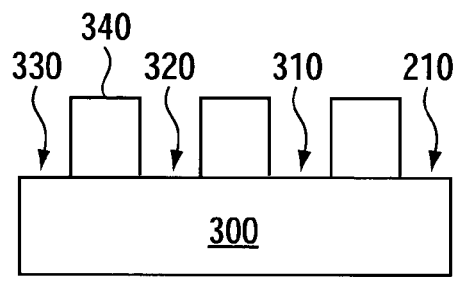
FIG. 3a is a side view of a mold, in accordance with one embodiment of the invention.
Figure 3B:
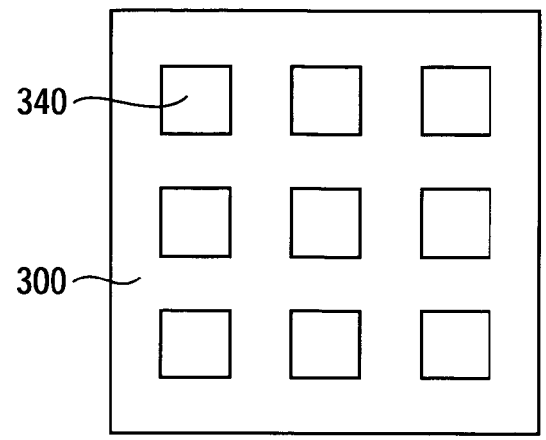
FIG. 3b is a top view of a mold, in accordance with one embodiment of the invention.

Referring to FIG. 3a, the mold 300 is shown completed, having open spaces 210, 310, 320, and 330 representing areas of the pattern. Teeth in the mold, such as tooth 340, may be used to stamp down the impressions of the pattern to form the template. FIG. 3b provides a top view of the mold 300, showing tooth 340 as one of nine teeth on the mold 300.

Figure 4:
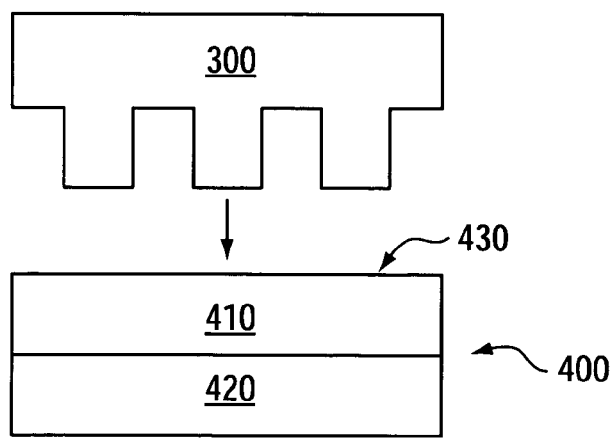
FIG. 4 is an illustration of a mold being used to stamp out a pattern on a resist layer, in accordance with one embodiment of the invention.

Referring to FIG. 4, the mold 300 is shown in a position to stamp out a pattern on the top surface 430 of a resist layer 410 of a wafer structure 400. The wafer structure 400 consists of a resist layer 410 above a substrate 420. In operation, a mold may be pressed into the resist layer 410, forming a template. This operation may be repeated, providing multiple templates.

Figure 5:
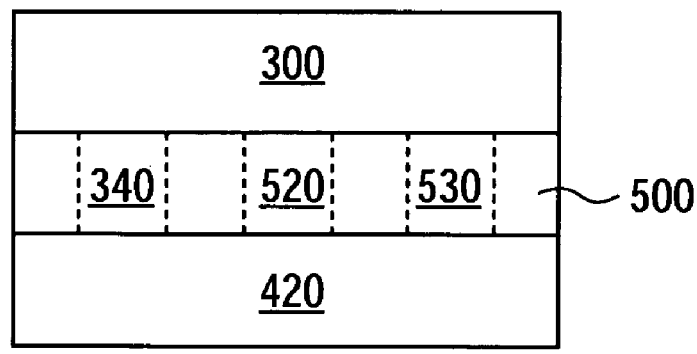
FIG. 5 is an illustration of a template interposed between a mold and a substrate, in accordance with one embodiment of the invention.

Referring to FIG. 5, the resist layer 410 of FIG. 4, now pressed into a template 500, is shown interposed between the mold 300 and the substrate 420. Teeth 340, 520, and 530 of the mold are shown hidden with dashed lines in the template 500. The resist layer 410 (shown in FIG. 4) has been stamped down in FIG. 5 in areas corresponding to the locations of the mold's 300 teeth.

Figure 6:
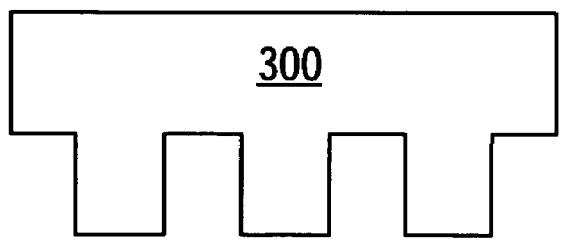
FIG. 6 is an illustration of a mold being removed from a structure, in accordance with one embodiment of the invention.
Figure 6:
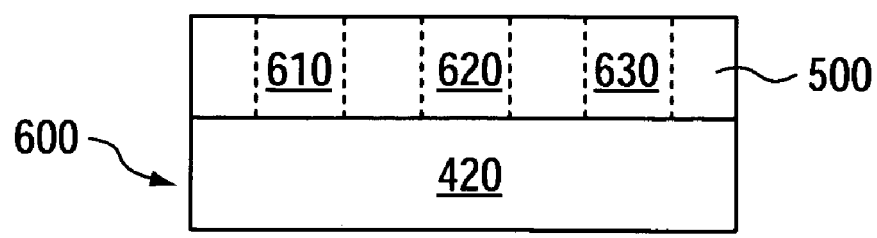

Referring to FIG. 6, the mold 300 is shown being removed from template/substrate structure 600. Template/substrate structure 600 is comprised of template 500 atop substrate 420. The template 500 now contains the nanoscale pattern stamped by mold 300 in the resist layer 410 (shown in FIG. 4). Open spaces 610, 620, and 630 are shown in the template hidden with dashed lines. The open spaces were formed by teeth 340, 520, and 530 (shown in FIG. 5). Six other spaces are formed in the resist layer 410, but are not shown in this view.

Figure 7:
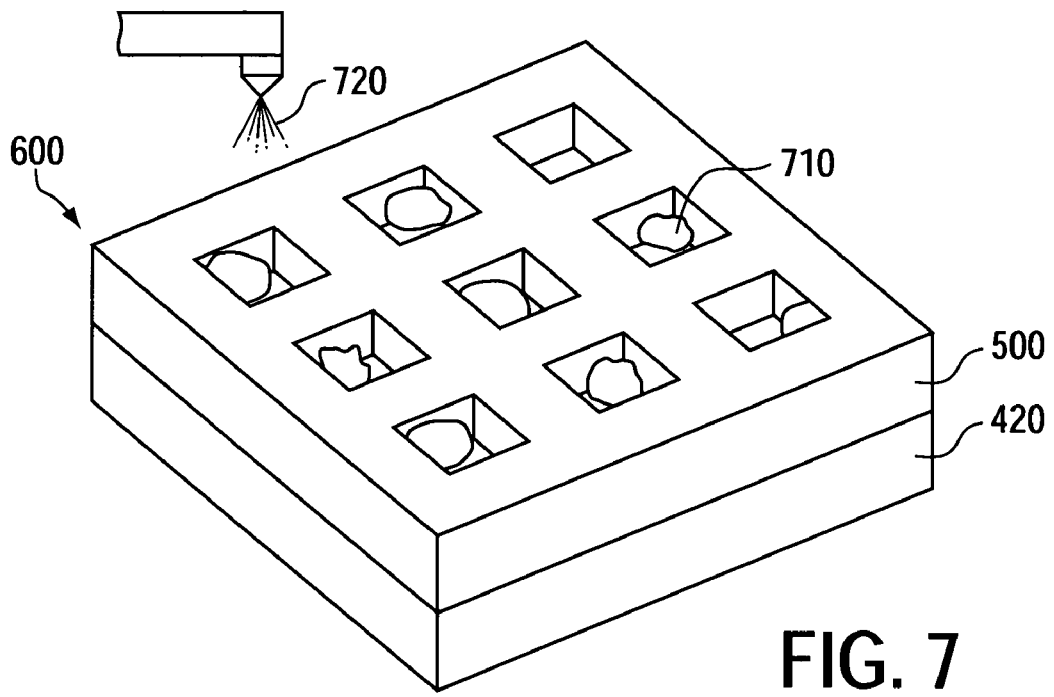
FIG. 7 is an illustration of residual resist material being removed from a template and a substrate, in accordance with one embodiment of the invention.

Referring to FIG. 7, a perspective view of the template/substrate structure 600 is shown with all nine openings visible. Also visible is residual resist material 710 in the template openings. Residual resist material on the substrate 420 that deviates from the desired template form is removed from the template 500 and substrate 420 with a chemical wash 720. In other embodiments, the residual resist material could be removed by other alternate means, including a brief exposure to an oxygen plasma.

Figure 8:
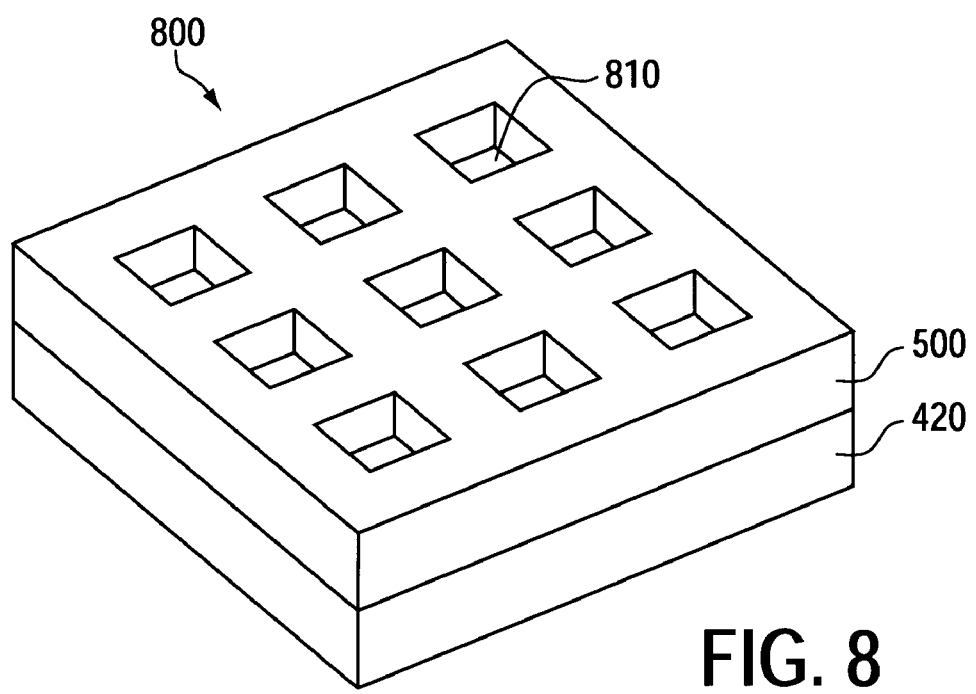
FIG. 8 is an illustration of a template attached to a substrate, in accordance with one embodiment of the invention.

Referring to FIG. 8, the template/substrate combination 800 composed of the template 500 attached to the substrate 420 is shown after the residual resist is removed from the template openings. The template 500 provides a nanoscale pattern above the substrate 420. In one embodiment, a template is used to fabricate ordered patterns having nanoscale features on a substrate. In one embodiment, the nanoscale pattern of openings is formed by equally spaced openings, such as opening 810. In other embodiments, the patterns could form any desired design, including periodic, non-periodic, or other patterns. For example some dimensions of template openings may be typically 20×20×20 nanometers in volume or generally between 1 and 100 nanometers.

Figure 9:
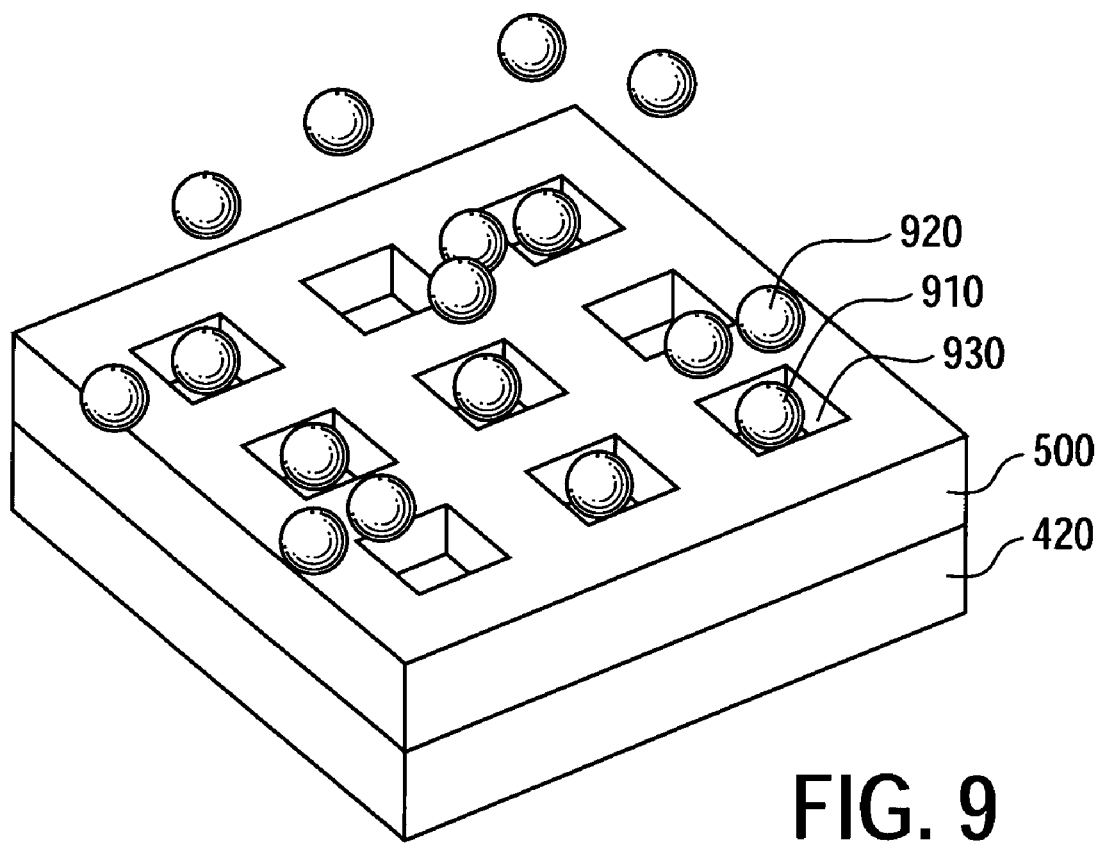
FIG. 9 is an illustration of nanoscale objects being deposited into the openings of a template, in accordance with one embodiment of the invention.

Referring to FIG. 9, nanoscale objects are introduced to the template 500. As shown, the template 500 is configured with openings to receive the nanoscale objects. Some nanoscale objects will enter into the openings of the template 500. For example, nanoscale object 910 enters into template opening 930. Other nanoscale objects may sit on top of the template's outer surface, such as, nanoscale object 920. In this embodiment at least one of the nanoscale objects remains outside of the openings. Nanoscale objects can continue to be introduced until all or substantially all of the openings of the template have received a nanoscale object. Nanoscale objects remaining outside of the openings on the surface of the template 500, may then be then removed with a brush or by other suitable means such as, for example, a chemical wash. In one embodiment, the nanoscale objects are applied about the template in a manner to cause the nanoscale objects to contract or be proximal to the substrate surface.

In the embodiment described in FIG. 9, individual nanoscale objects are assembled using the template 500. These nanoscale objects may comprise, for example, nanowires; nanoparticles; nanorods; nanotubes; fullerenes; viral particles; polynucleic acid; polypeptides; proteins; DNA; or liquids. Liquids can be solvents or mixtures of all of the above. For example, dispensing of nano-objects may take place in solution rather than gas or in a vacuum. Also, small (nano-size) droplets of liquid itself could be the nano-objects that are positioned in the holes. Examples include water over unwetted surfaces, liquid metals, and other objects in a liquid or in a liquid state, such as solutions or suspensions of molecules. In additional embodiments, other materials may be deposited into a template created by imprint lithography. In one embodiment, for example, a film may be applied in the template openings. The film could be configured to coalesce when heated, thereby forming nanoparticles of diameters substantially smaller than the size of the template openings. In another embodiment, the nanoscale objects deposited into the template openings could be composed of a molecular film. Uses of nanopatterned molecular films include any of the uses of molecular films, here applied at the nanoscale. In yet another embodiment, the nanoscale objects deposited into the template openings may be electroplated films. In yet another embodiment, the nanoscale objects may be comprised of a layer of organic or inorganic chemicals, including elements, mixtures, compounds, or other substances. In another embodiment, the nanoscale objects may be configured for molecular attachment to a target molecule.

In the embodiment of FIG. 9, the openings such as opening 930 are cubic. However, in other embodiments the openings of the template could form different shapes, including openings that are elongated, equiaxed, triangular, cylindrical, or other shapes. The size and shape of each template opening is predetermined and can vary with respect to the other template openings. The size and shape of each template opening could be chosen according to appearance of the opening on the template surface as well as the way the opening protrudes down through the resist layer to the substrate. The size and shape of a template opening could also be chosen to accommodate a particular size and/or shape of a nanoscale object, or to accommodate a plurality of nanoscale objects. The size and shape of a template opening could also be chosen so as to exclude nanoscale objects of a particular size range, for example, in a manner to allow small particles to enter, while at the same time to prevent large particles from entering.

The size, shape, and position of a template opening may further be chosen to accommodate a predetermined number of nanoscale objects substantially arranged in a line with a predetermined orientation or in a square arrangement or any other predetermined arrangement. In yet still another embodiment, the size and shape of the openings may be chosen to accommodate nanoscale objects in a predetermined range of orientation coordinates. For example, a square template opening with edge lengths chosen to be approximately twice the diameter of a nanoparticle can be used to accommodate four nanoparticles in a square arrangement. The square arrangement is difficult to achieve by other means because like-sized objects will most commonly arrange themselves on triangularly arranged coordinates by natural processes. The size and shape of the openings may further be chosen to have multiple levels with different-sized openings at different levels. Examples are illustrated below. The size and shape of the openings may be chosen to accommodate nanoscale objects at different levels and/or layers in an opening.

In the embodiment described in FIGS. 8 and 9, nine openings are shown in template 500. However, it is noted that the number of openings in the template is a design parameter and can be varied. Additionally, the shape and location of each opening in the template are also design parameters and can be independently varied.

In other embodiments, the size and shape of the template openings may be chosen to accommodate a plurality of nanoscale objects, or a specific maximum or minimum number of nanoscale objects or fewer. The nanoscale objects could be put on the template using well known methods including Langmuir-Blodgett, self-assembly, evaporation, electrodeposition, electroless deposition, dipping, spraying, physical bonding, or chemical bonding.

Figure 10:
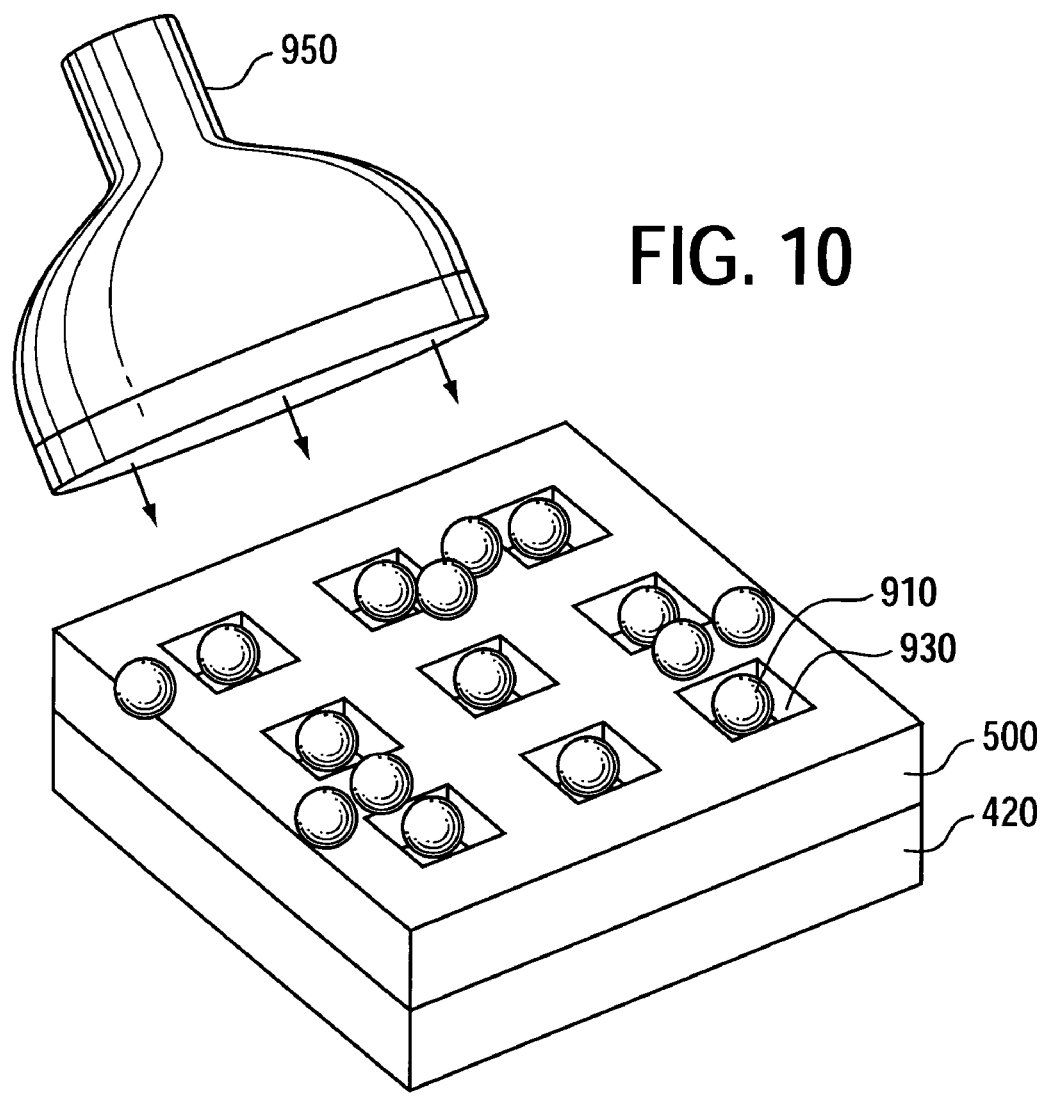
FIG. 10 is an illustration of a surface of a template being brushed, in accordance with one embodiment of the invention.

Referring to FIG. 10, once the openings 930 of the template 500 have been filled with objects 910, any objects remaining on the surface of the template 500 may be removed by a chemical washing, scrubbing, or by a process analogous to brushing. The brush 950 may be configured to remove the objects from the top surface, outside the openings of the template, as well as to aid in placing objects into the openings of the template 500.

Figure 11:
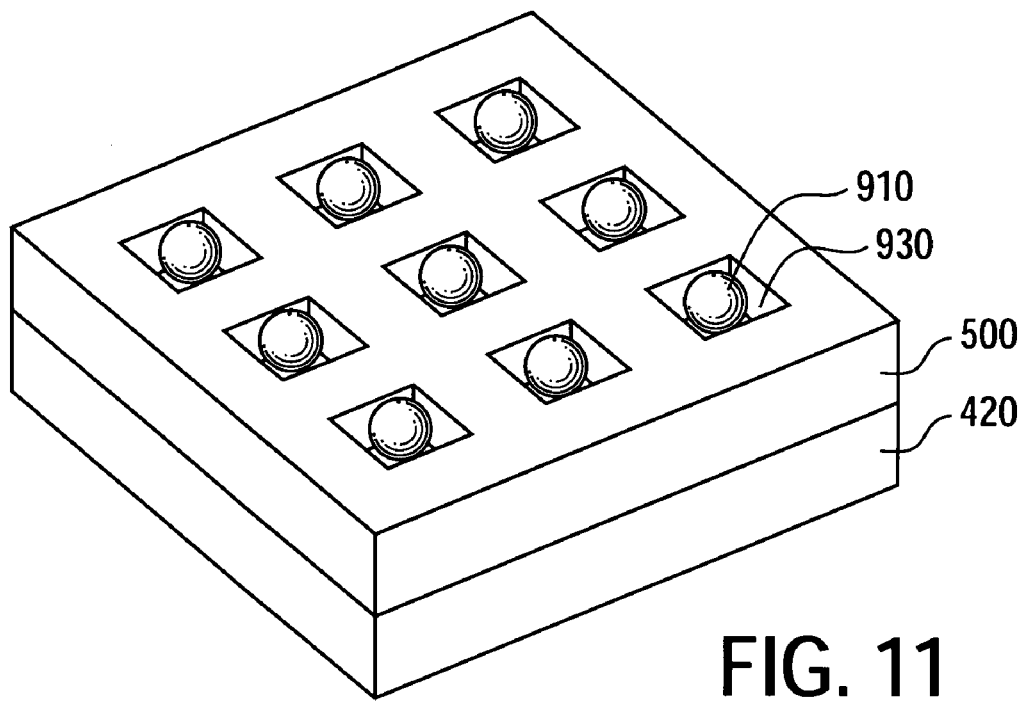
FIG. 11 is an illustration of a substrate and a template, where the openings of the template are filled with objects, in accordance with one embodiment of the invention.

FIG. 11 illustrates the template 500 and substrate 420 once the openings 930 of the template 500 have been filled with objects 910 and after any objects outside the openings have been removed. Though all of the openings are shown filled, in practice, the openings might not all be filled. The accuracy of the depositions may depend on a given application. In this embodiment, the nanoscale objects adhere naturally to the substrate. In other embodiments, adhesion of the nanoscale objects to the substrate may be enhanced via the use of chemical bonding, adhesives, or thermal treatment.

Figure 12:
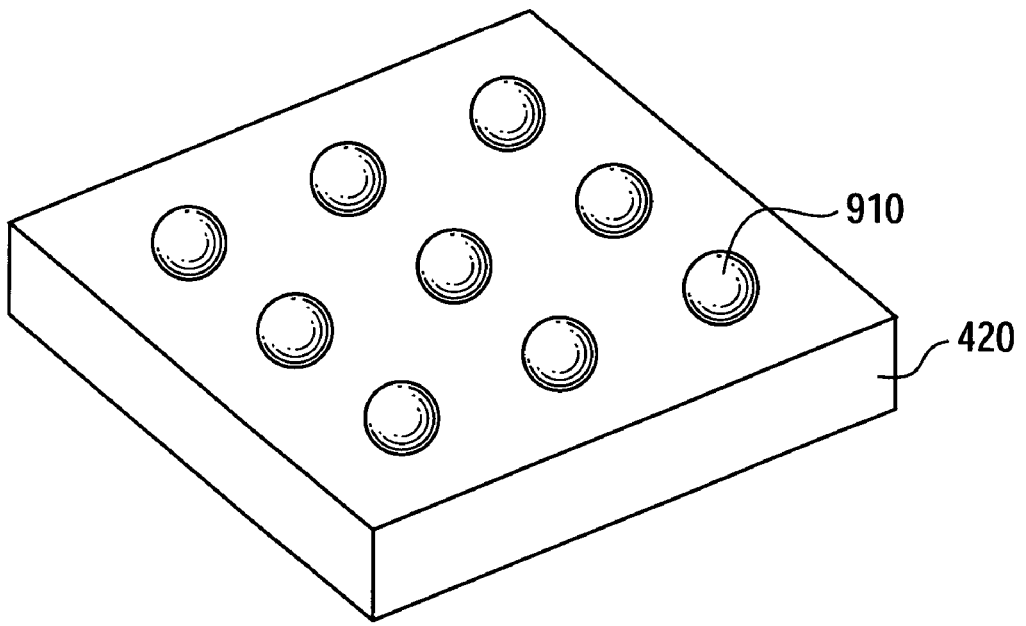
FIG. 12 is an illustration of nanoscale objects on a substrate, in accordance with one embodiment of the invention.

Referring to FIG. 12, once the nanoscale objects have been placed into the openings of the template 500, the template 500 may be removed by a chemical washing, for example. The nanoscale objects, such as nanoscale object 910, would remain on the substrate 420 at the locations and orientations dictated by the template design. The nanoscale objects remain in place due to the interaction between the nanoscale objects and the substrate 420 and/or the resist.

Figure 13:
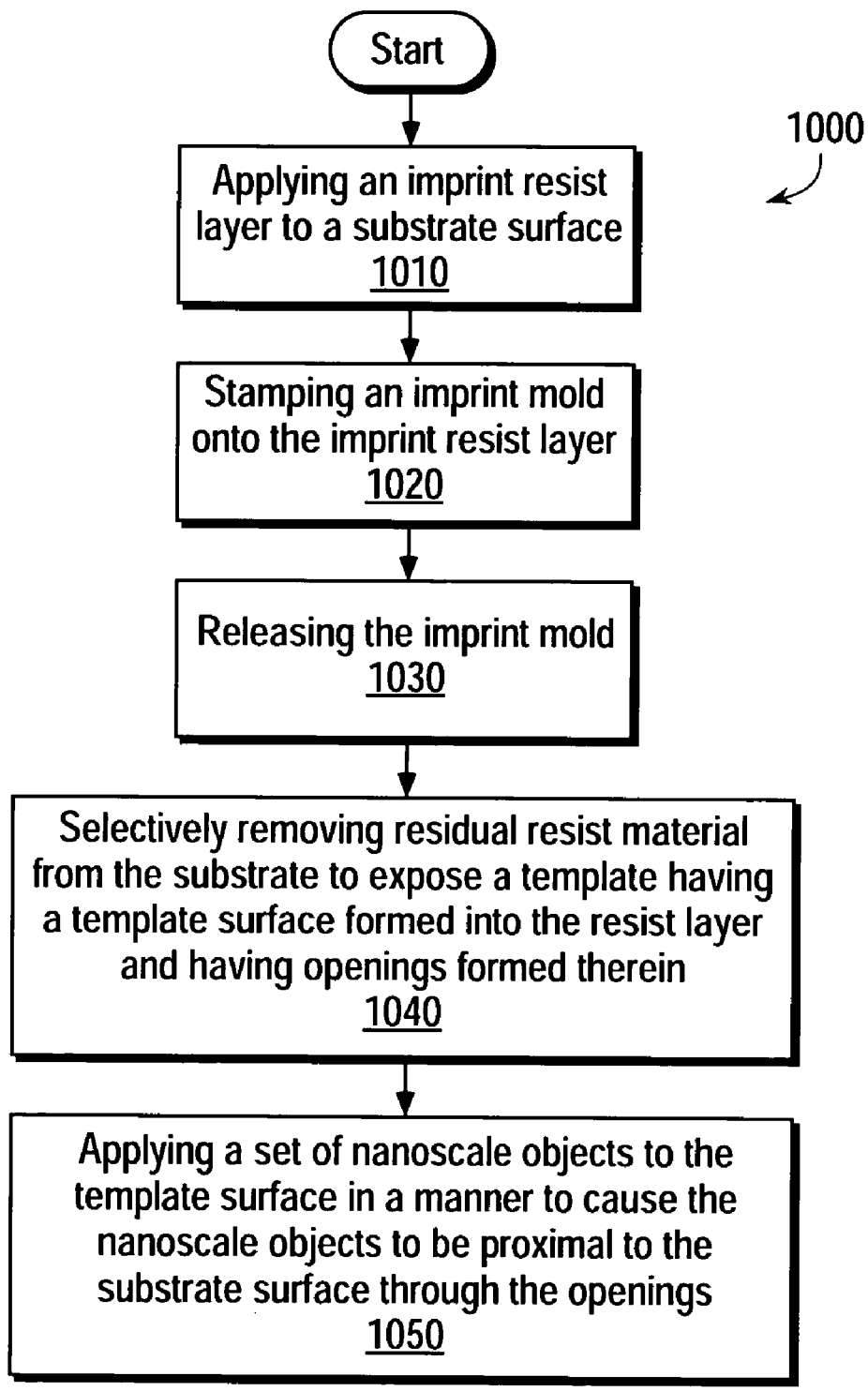
FIG. 13 is a flowchart illustrating a process for a method of using a template to fabricate ordered patterns of nanoscale objects on a substrate.

Referring to FIG. 13, a process according to one embodiment of the invention is illustrated in flow chart 1000. The process provides a method of using a template to fabricate ordered patterns of nanoscale features on a substrate. Though this process is described in the order of the steps illustrated in FIG. 13, embodiments of the invention are not necessarily limited to this order. At the start of the process, a layer of resist material is applied to a substrate surface in step 1010. The resist layer is used to create a template over the substrate. The resist layer may be composed of any resist material suitable for use in imprint lithography. The example discussed above in connection with FIG. 4 provides a wafer structure 400 including a resist layer 410 above a substrate 420. Embodiments of the invention are not limited to the use of resist material for the template, but extends to any material that may be configured to accommodate nanoscale objects.

Next, in step 1020, a mold (e.g., the mold 300) is stamped onto the resist layer. As discussed in connection with FIG. 2 above, a wafer 200 is used in the creation of a patterned mold having nanoscale features. The mold is patterned with nanoscale features. This pattern is to be transferred to the resist layer. The stamping may be performed by various methods, such as, for example, by a step and flash lithographic method.

The pattern of nanoscale features can be predetermined and have many different forms. In one embodiment, the pattern may contain at least one periodic pattern or at least one non-periodic pattern. In further embodiments, the pattern may be symmetrical or nonsymmetrical, or may contain combinations of different patterns.

Next, in step 1030, the imprint mold is released. FIG. 7, discussed above, illustrates a template after an imprint mold has been released. The template illustrated also shows residual resist material left over from earlier steps in the process.

In step 1040, residual resist material is selectively removed from the template openings to expose the substrate. The result is a template having a template surface formed into the imprint resist layer and having openings formed therein. The openings are of a nanoscale size, and are ordered in a pattern with respect to at least one of a group consisting of size, shape, orientation, pattern, and position. As illustrated in FIG. 8, template 500 exposes selected portions of the substrate's 420 surface. Only a residual portion of the resist layer is selectively removed from the substrate surface. In one embodiment, the openings are ordered in a pattern with respect to at least one of a group consisting of size, shape, orientation, path, and position, and may also be of one or more predetermined sizes or one or more predetermined shapes. The openings are further positioned in one or more predetermined orientations.

In step 1050, a set of nanoscale objects is applied to the template surface in a manner to cause the nanoscale objects to be proximal and/or contact the substrate surface through the openings. As discussed above, in connection with FIG. 9, nanoscale objects are shown being applied to the template 500. In one embodiment, the nanoscale objects are applied about the template in a manner to cause the nanoscale objects to contact or be proximal to the substrate surface. Some of the nanoscale objects will move into the openings of the template 500 and will be proximal to or contact the substrate surface exposed through the openings.

Once the objects have been deposited, linear growth of the nanoscale objects can be initiated on the substrate surface. The template openings may serve as a guide for this growth. The nanoscale objects can be used for molecular attachment. In one embodiment, the nanoscale objects are comprised of DNA, polynucleic acid, polypeptide, or a layer of chemistry. The DNA, polynucleic acid, polypeptides, or layer of chemistry can further be used for chemical sensing applications or as scaffolding material to construct complicated biomolecular architectures. In one embodiment of the method, a second set of nanoscale objects is deposited to a surface of the template. The first set of nanoscale objects may be of a different size than the second set of nanoscale objects. In one embodiment, the second set of nanoscale objects is applied about the template in a manner to cause the second set of nanoscale objects to contact or be proximal to the first set of nanoscale objects.

The resulting product from process 1000 can be used as shown in FIG. 11, or the template can be removed from the substrate surface as illustrated in FIG. 12. The process provides a method of using a template to fabricate ordered patterns of nanoscale objects on a substrate. The process can further be applied as discussed above. Resulting structures from process 1000 may be used to produce circuit components on a nanoscale as discussed below.

In the embodiment described above, the nanoscale objects in FIG. 12 are simple objects. However, in other embodiments the nanoscale objects created can be more complex. According to the invention, nanoscale circuit materials and components such as resistors, transistors, capacitors, and other components can be formed accordingly, and their number, size, shape, pattern, orientation, and position can be controlled.

In one embodiment, a structure can be formed using nanoscale objects to provide a simple electrical connection to a substrate. In further embodiments, structures can be formed that provide electrical function other than simple electrical connection. Examples include rectification, Coulomb blockade, switching, amplification, memory, and impedance. The electrical function can be provided by the nanoscale objects in conjunction with any elements to which they are connected or proximal.

One example of nanoscale objects created with the templates is nanoscale wires. Templates can be used to grow nanoscale wires from the surface of silicon at predetermined positions. In this process, the silicon surface is seeded through the template such that the seed material is exposed to the substrate surface. Then catalysis is used in a vacuum process to initiate the growth of wires. With this process, the wires grow outwardly or substantially perpendicular to the surface of the silicon substrate. During the processing of the wire, dopants can be used to build wires with p- and n-type dopants.

In yet another embodiment, the nanoscale objects created with the templates can be nanotubes. Growth seeds for nanotubes can be planted on substrates by placing them into the openings of a template. The template may then be removed, leaving the tube seeds in place on the substrate for growth. In nanotubes, the conductivity is high and such structures can be used effectively as components for nanocircuits. Using the template, nanotubes can be placed in predefined positions on a surface so that local nanotube growth can be controlled.

Figure 14:
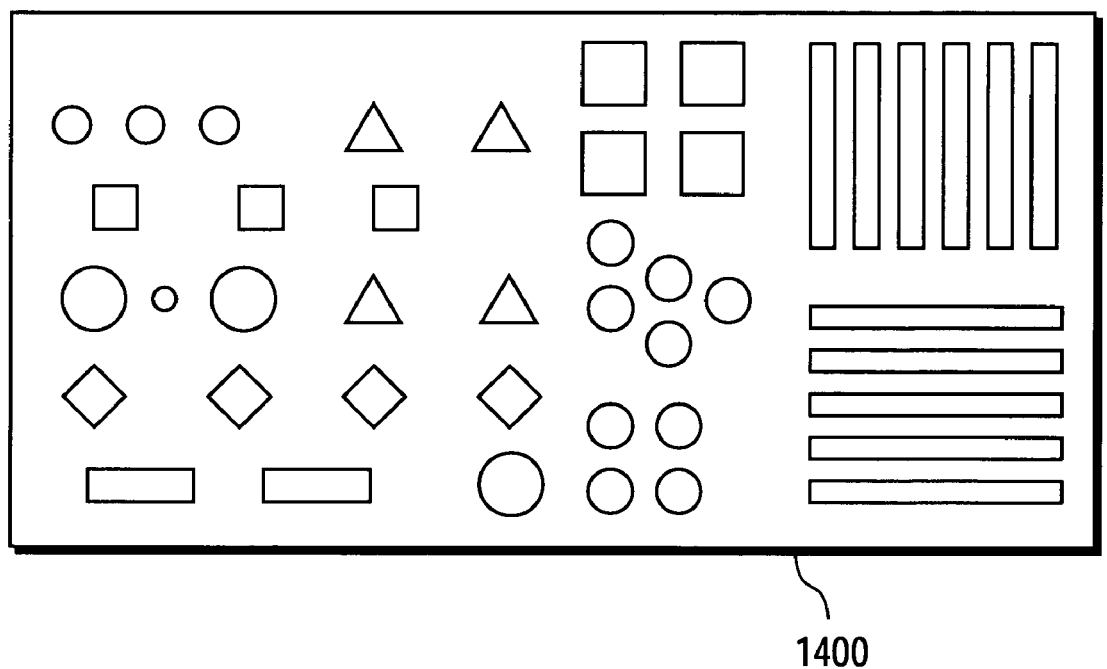
FIG. 14 is an illustration of a template, in accordance with one embodiment of the invention.

To achieve the different applications for nanoscale components, templates can be created in many configurations. For example, a template with nanoscale openings can be created with a predetermined pattern that is symmetrical, nonsymmetrical, periodic, nonperiodic, or some other pattern. The nanoscale openings can also be varied. For example, the nanoscale openings of the template can be of one or more predetermined sizes or shapes, and positioned in one or more predetermined orientations. Referring to FIG. 14, an example of a template 1400 is illustrated having a pattern where the nanoscale openings are of different sizes and patterns. Objects on the left side of FIG. 14 are non-systematic and of varying shape, size, orientation, spacing, and arrangement as can be produced by the present invention. On the right side of the template 1400 are more orderly structures that here can be produced, such as the two vernier-like structures set at orthogonal orientations and the two arrays of circles at nonorthogonal orientations.

Figure 15:
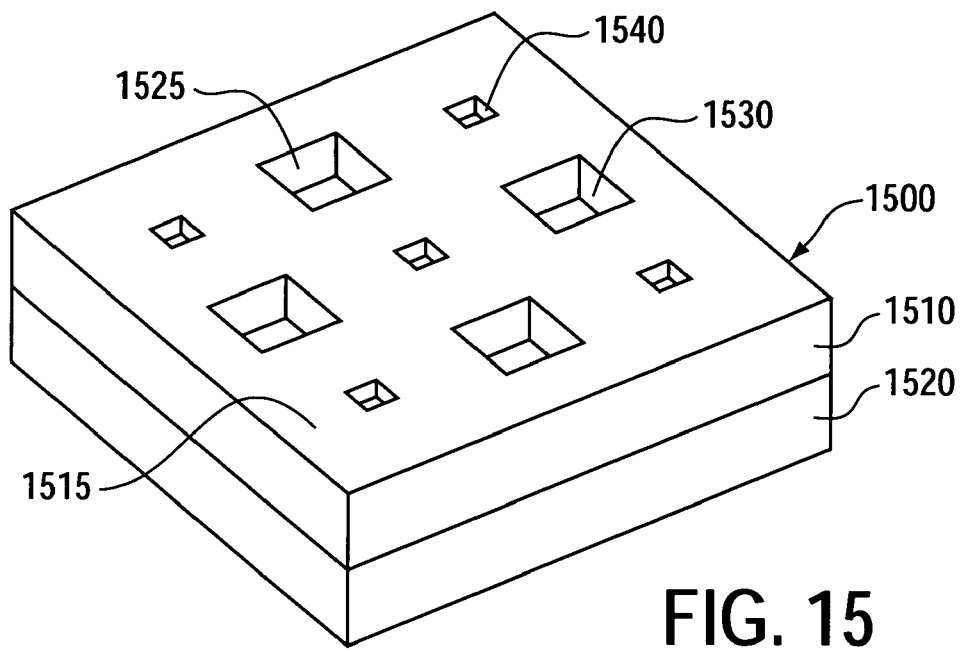
FIG. 15 is an illustration of a template above a substrate, in accordance with one embodiment of the invention.

FIGS. 15 through 20 illustrate a process for combining different sized nanoscale features on a single template. FIG. 15 illustrates a template having a periodic pattern formed by openings of two different sizes. Structure 1500 comprises a template 1510 above a substrate 1520. The template 1510 provides a pattern where the openings are of two different sizes and form a periodic pattern. Larger openings, such as opening 1530, provide large rectangular shaped voids in the template 1510. Smaller openings, such as opening 1540, provide smaller rectangular shaped voids in template 1510.

Figure 16:
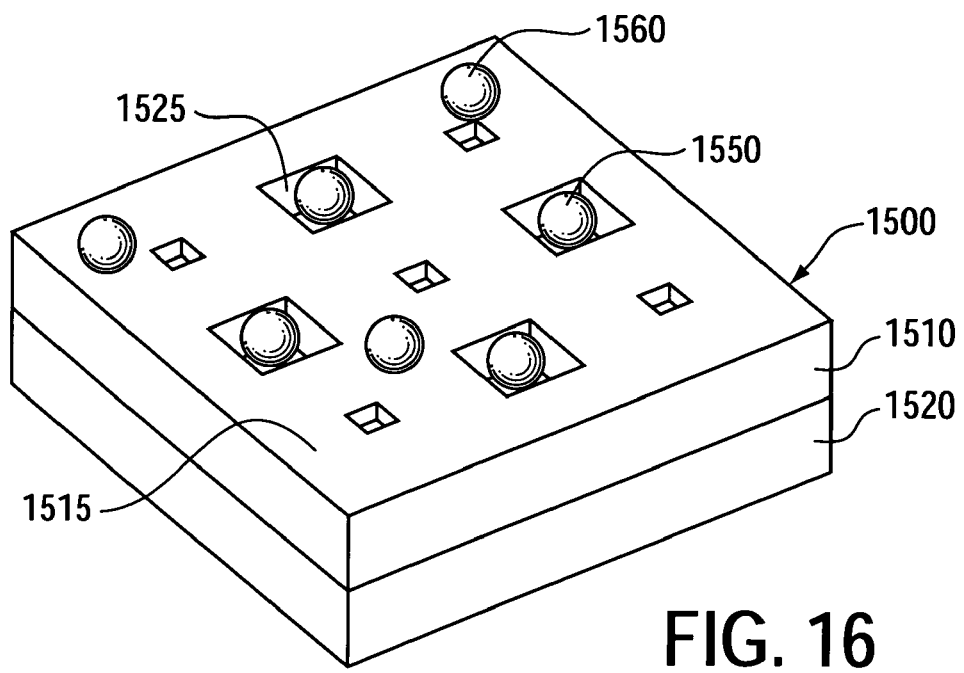
FIG. 16 is an illustration of nanoscale objects applied to a template above a substrate, in accordance with one embodiment of the invention.
Figure 17:
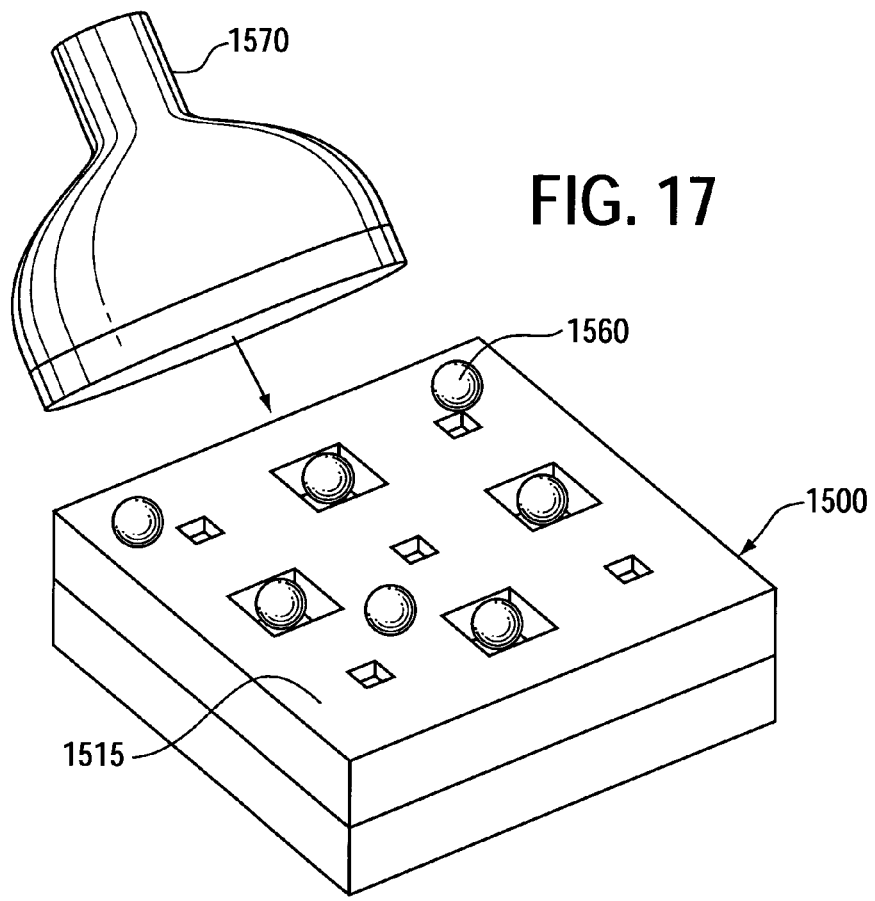
FIG. 17 is an illustration of a substrate and a template, where nanoscale objects are being brushed off the template, in accordance with one embodiment of the invention.

Referring to FIG. 16, a set of nanoscale objects each having a size corresponding to the larger openings is applied to the template 1510 in a manner to cause the objects to contact or be proximal to the substrate surface 1545 through the larger openings, such as opening 1530. Some of the nanoscale objects will enter into the openings of the template 1510 above the substrate surface 1545. For example, an object 1550 is shown in one of the larger openings, opening 1530. Other objects may sit on the template surface 1515, such as object 1560. Objects can continue to be applied until all or substantially all of the larger openings of the template 1510 are filled. Large objects, such as object 1560, remaining on the template surface 1515 may then be brushed from the template surface 1515 with a brush 1570, as shown in FIG. 17. The act of brushing may also aid the objects on the template surface 1515 to fall into empty openings.

Figure 18:
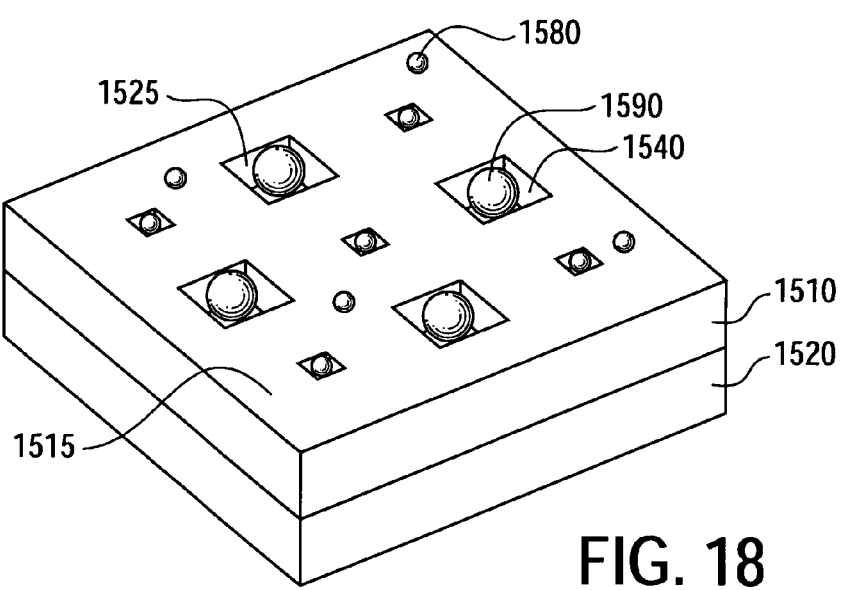
FIG. 18 is an illustration of nanoscale objects applied to a template above a substrate, in accordance with one embodiment of the invention.
Figure 19:
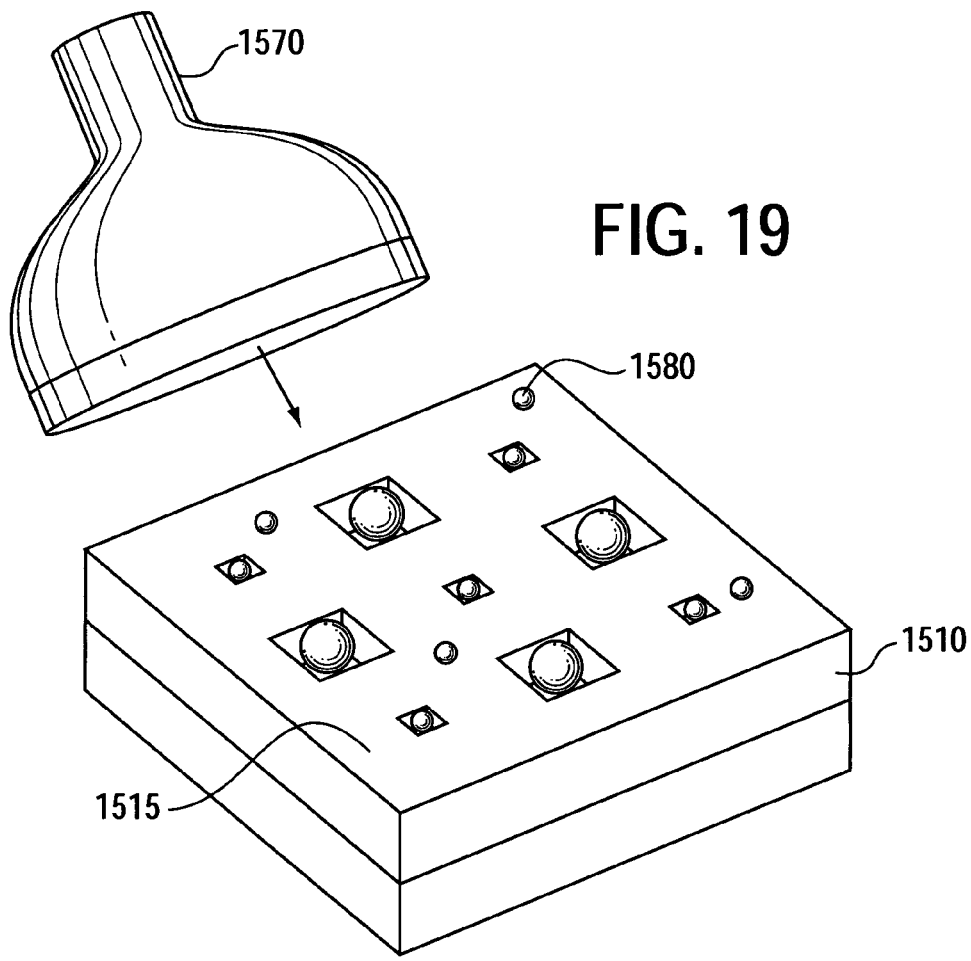
FIG. 19 is an illustration of a substrate and a template, where nanoscale objects are being brushed off the template, in accordance with one embodiment of the invention.
Figure 20:
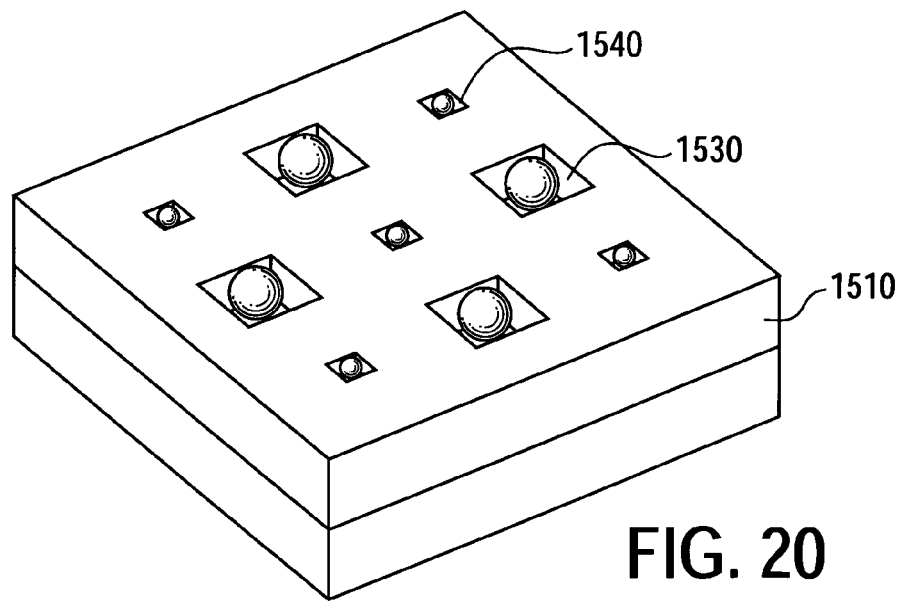
FIG. 20 is an illustration of a substrate and a template, where the openings of the template are filled with objects, in accordance with one embodiment of the invention.

Referring to FIG. 18, a smaller set of nanoscale objects is applied to the template 1510 in a manner to cause the objects to contact the substrate surface 1545 through the smaller openings, such as opening 1540. Some of the nanoscale objects will enter into the smaller openings of the template 1510 above the substrate surface 1545. For example, an object 1590 is shown in one of the smaller openings, opening 1540. Other objects may sit on top of the template surface 1515, such as object 1580. Objects can continue to be applied until all of the smaller openings of the template 1510 are filled. Small objects, such as object 1580, remaining on the template surface 1515 may then be brushed off the template surface 1515 with a brush 1570, as shown in FIG. 19. Similar to the large objects, the brushing process may aid in helping the small objects into the smaller openings of the template 1510. Referring to FIG. 20, the template 1510 is shown with all of the small openings, such as opening 1540, and larger openings, such as opening 1530, filled with objects. The template 1510 may then be removed (not shown). Alternatively, the template 1510 may be left in place as shown in FIG. 20.

Figure 21:
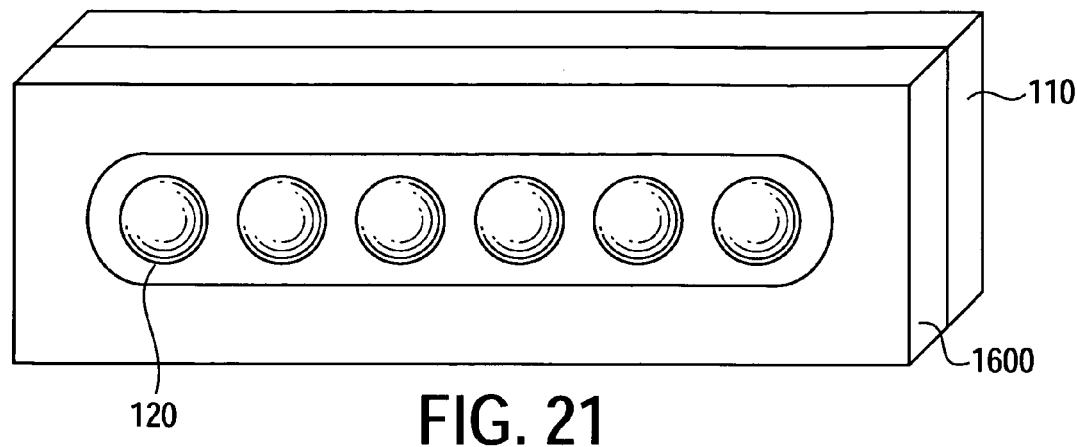
FIG. 21 is an illustration of a substrate and a template, where the template contains an opening, in accordance with one embodiment of the invention.

Referring to FIG. 21, a template is shown for creating the structure provided in FIG. 1. The template 1600 is placed atop a substrate 110. The template 1600 contains an opening that accommodates six nanoscale objects 120 in a substantially straight line. In one embodiment, the structure may be used as a connection link.

Figure 22:
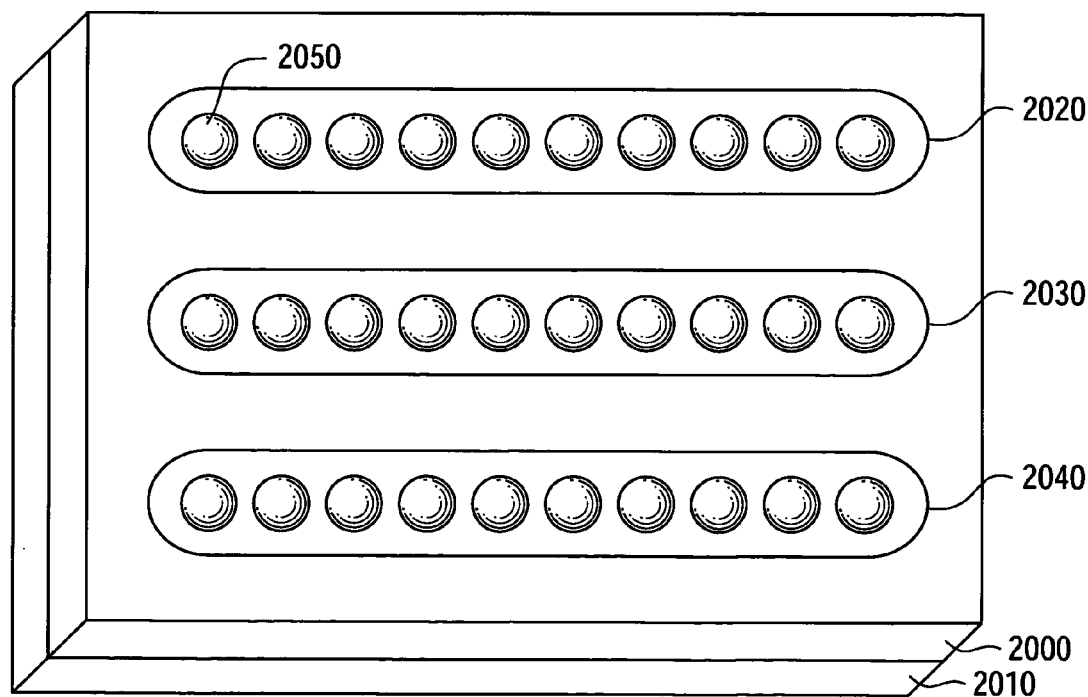
FIG. 22 is an illustration of a substrate and a template, where the template contains three openings, in accordance with one embodiment of the invention.
Figure 23:
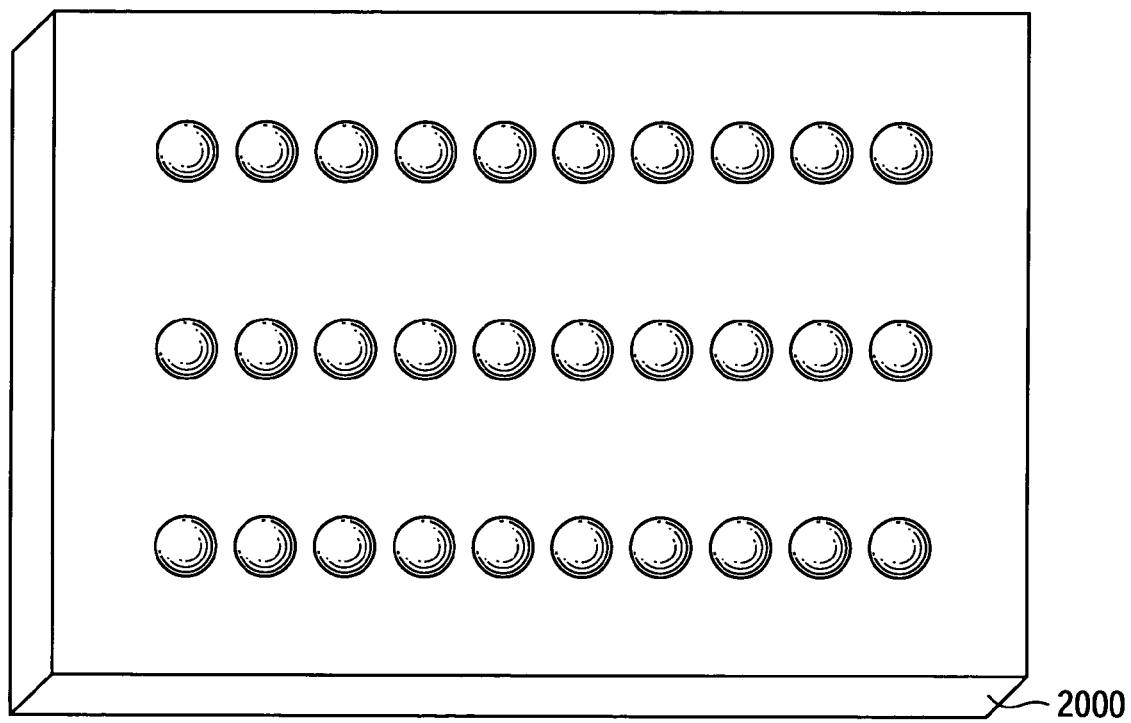
FIG. 23 is an illustration of nanoscale objects on a substrate, in accordance with one embodiment of the invention.

In yet another embodiment, FIG. 22 illustrates a template 2000 and substrate 2010. The template 2000 contains three openings 2020, 2030, and 2040. Each opening can accommodate ten nanoscale objects in three substantially straight and substantially parallel lines. Ten nanoscale objects 2050 are shown in opening 2020. FIG. 23 illustrates the objects 2050 in place with the template 2000 removed from the substrate 2010 (shown in FIG. 22). The nanoscale objects remain on the substrate 2010 (shown in FIG. 23). The nanoscale objects of the structure 2060 shown in FIG. 23 may be used as connections or wires or may be crossed with other structures to form a grid.

Figure 24:
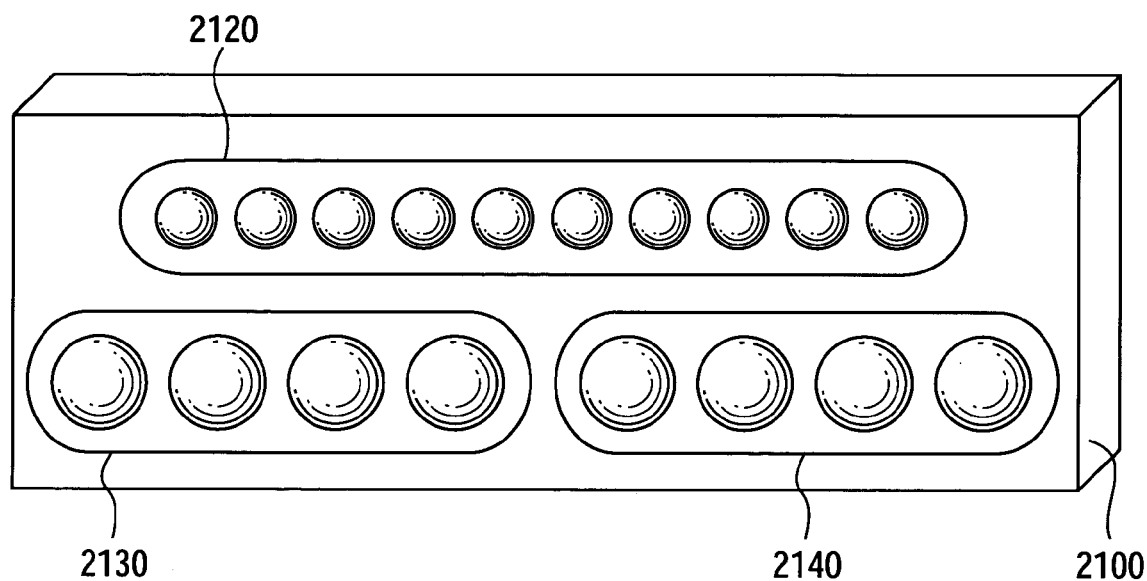
FIG. 24 is an illustration of a substrate and a template, where the template contains three openings, in accordance with one embodiment of the invention.

Referring to FIG. 24, another template 2100 is illustrated. The template 2100 contains three openings 2120, 2130, and 2140. Opening 2120 can accommodate ten nanoscale objects in a substantially straight line. Openings 2130 and 2140 can accommodate four nanoscale objects of a relatively larger size in two substantially straight lines. Such a structure may be manufactured in the same manner as the structure illustrated in FIGS. 15-20, given the different sizes of the nanoscale objects.

Figure 25:
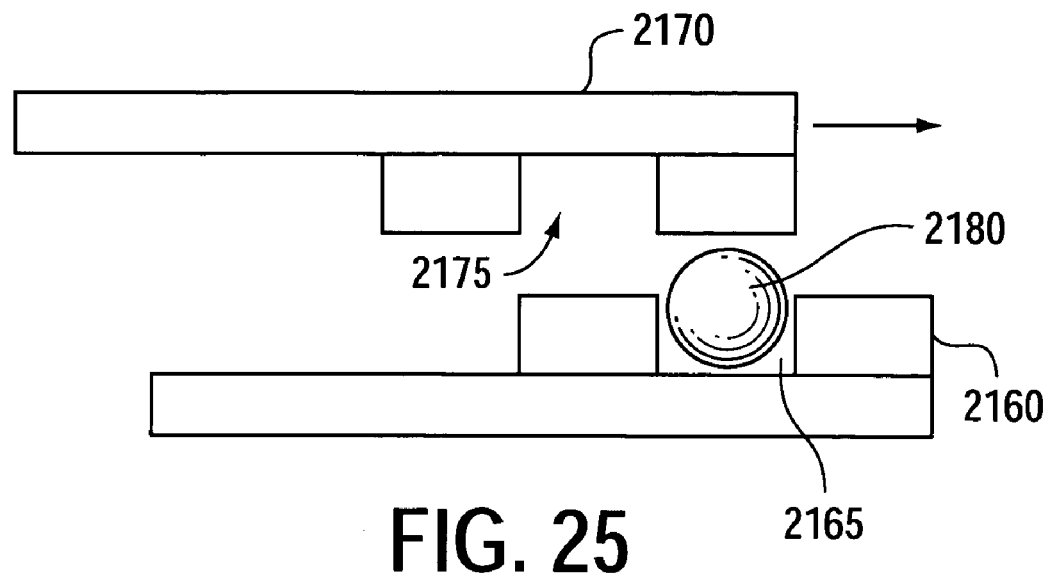
FIG. 25 is an illustration of a structure used to align two surfaces, in accordance with one embodiment of the invention.

In another embodiment, templates having nanoscale features are used to align two structures. FIG. 25 provides a side view of two templates 2160 and 2170. These templates are equal in size and shape. Both templates 2160 and 2170 have nanoscale openings 2165 and 2175 respectively. The nanoscale openings 2165 and 2175 are equal in size and located at the same relative position on both templates 2160 and 2170. In other embodiments, the nanoscale openings are not equal in size. The nanoscale openings 2165 and 2175 are shown facing each other. A nanoscale object 2180 is placed in the nanoscale opening 2165 of template 2160. The presence of the nanoscale object 2180 will facilitate in the alignment of the two templates 2160 and 2170 by providing a ball bearing function.

Figure 26:
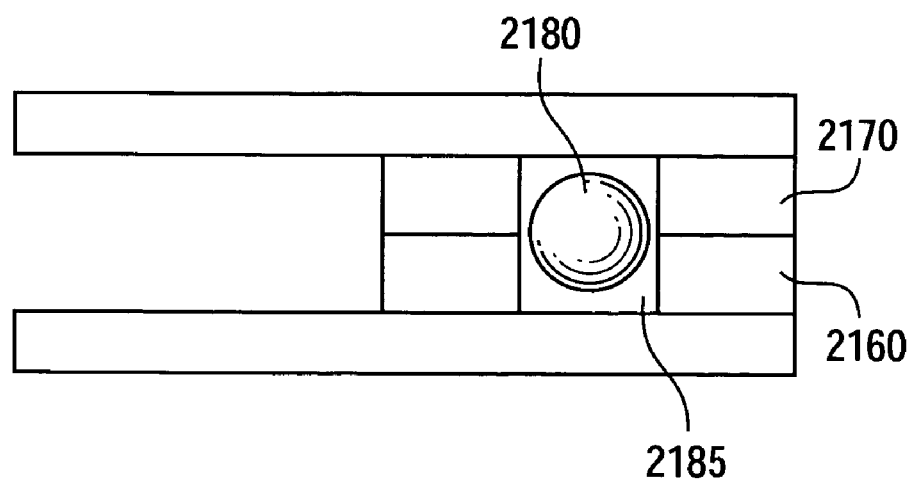
FIG. 26 is an illustration of a structure used to align two surfaces, in accordance with one embodiment of the invention.

FIG. 26 shows template 2170 positioned above template 2160 with the two nanoscale openings 2165 and 2175 (shown in FIG. 25) in alignment and creating opening 2185. In positioning the template 2170 above the template 2160 the nanoscale object 2180 provides a ball bearing function. During placement of template 2170 over template 2160, nanoscale object 2180 facilitates the alignment of the reciprocal nanoscale openings 2165 and 2175 (Shown in FIG. 25). As a result, the two templates can be conveniently aligned with respect to the location of their respective nanoscale openings. The nanoscale object 2180 holds the template 2170 in place, preventing it from moving out of alignment with template 2160. The described ball bearing feature in a nanoscale opening can be used to align a variety of structures. Thus, nanoscale objects can act as ball bearings with respect to aligning a template relative to a second template or another template. As the templates 2160 and 2170 are brought into alignment the nanoscale object 2180 forces the two nanoscale opening 2165 and 2175 to line up. Furthermore the two nanoscale openings stay lined up as the nanoscale object 2180 acts as an obstacle to prevent the templates from moving out of alignment. This feature can be used to align structures with the use of nanoscale openings and objects.

Another useful application of embodiments of the invention is to accomplish the layering of nanoscale objects. For example, the size and shape of nanoscale openings in a template may be configured to contain layers positioned at different levels. This feature would facilitate the layering of nanoscale objects or materials in a template.

Figure 27:
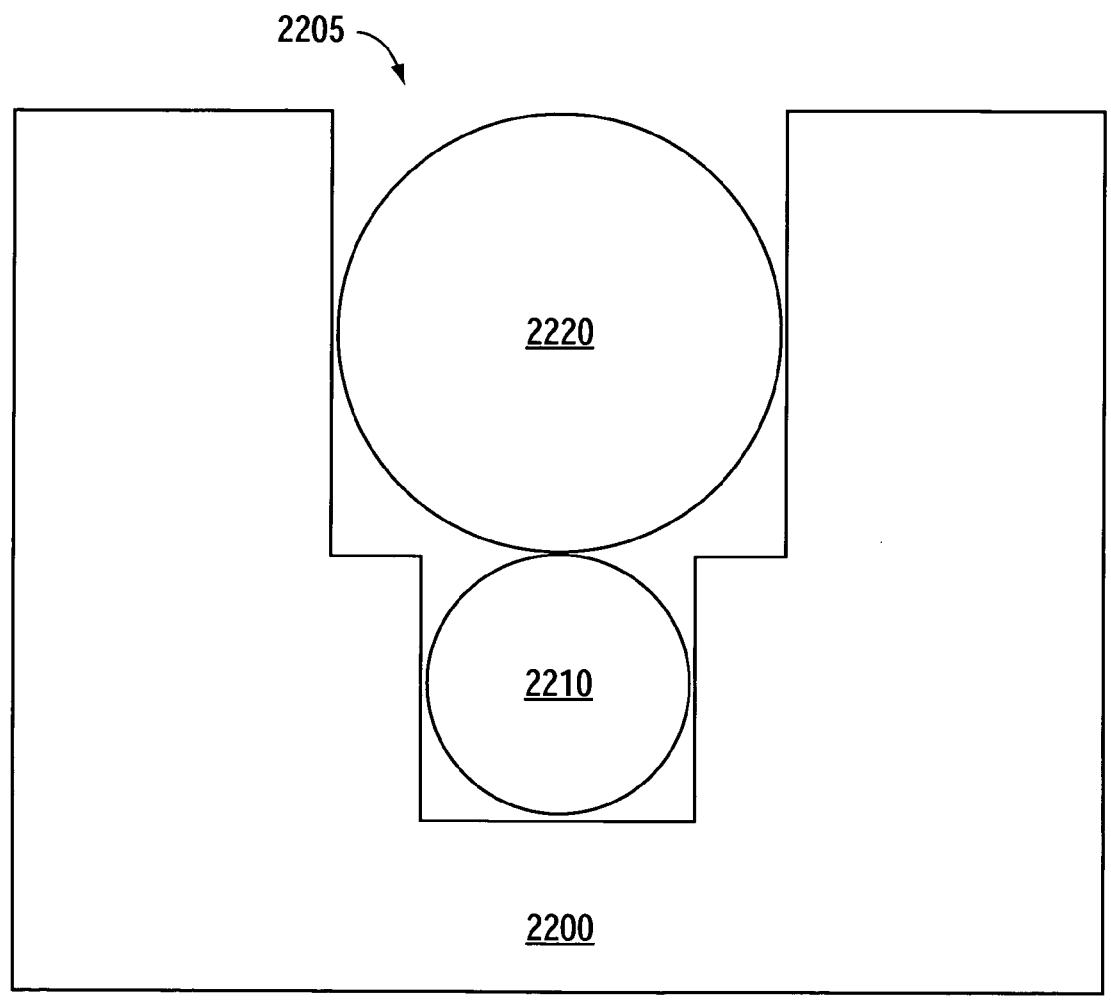
FIG. 27 is an illustration of a structure having a nanoscale opening that can accommodate two different sized nanoscale objects each on a different level, in accordance with one embodiment of the invention.

FIG. 27 provides a cross-sectional view of a template having a nanoscale opening that can accommodate two different-sized nanoscale objects each on a different level, in accordance with one embodiment of the invention. Template 2200 has a nanoscale opening 2205. The bottom level of the nanoscale opening 2205 contains nanoscale object 2210. The upper level of nanoscale opening 2205 contains nanoscale object 2220. The upper level of nanoscale opening 2205 is larger than the lower level and thus accommodates a relatively larger nanoscale object than the lower level of nanoscale opening 2205. One reason this embodiment is useful is because it makes it easier to accommodate smaller objects first and larger objects later.

Different materials could be used to fill each level in a multiple level nanoscale opening. This multiple level feature in a nanoscale opening could be applicable in different fields, such as, for example, semiconductor fabrication. In semiconductor fabrication, layering of different materials in substrates is useful. Only one nanoscale opening 2205 is shown in FIG. 27, however, multiple openings could be positioned in a template. Two levels are shown within the nanoscale opening 2205, but in other embodiments, more levels could be provided within an individual nanoscale opening.

Another useful application of embodiments of the invention is using nanoscale openings in a template to bridge two layers at different levels in an electrical circuit. When filled with conductive nanoscale objects such nanoscale openings can act as vias providing electrical connections through the template. Nanoscale objects can then be positioned in the vias created by the nanoscale openings of the template. Also, wires on different levels can be separated.

Figure 28:
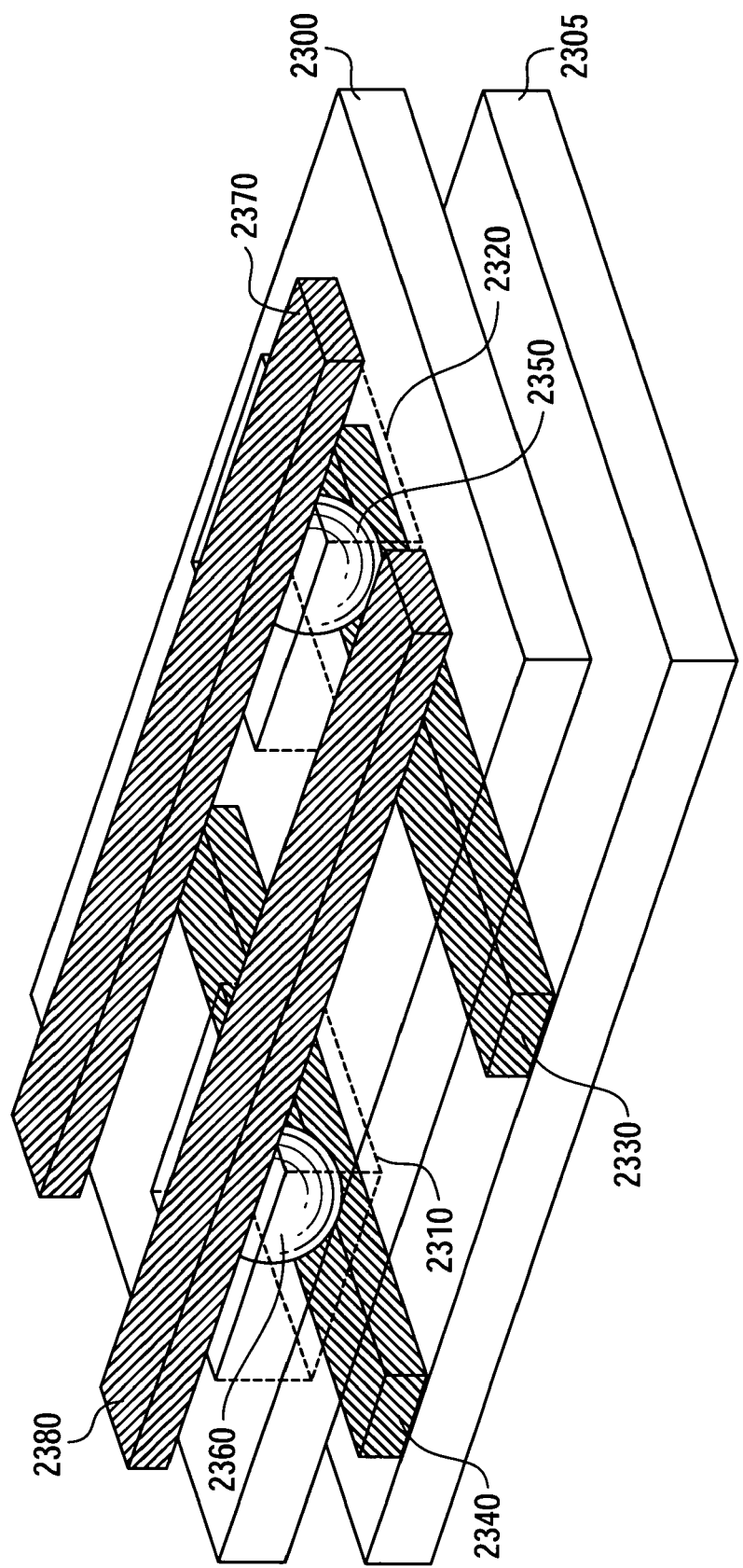
FIG. 28 is an illustration of a structure used to create electrical connections between different levels of electronic elements, in accordance with one embodiment of the invention.

According to embodiments of the invention, electronic devices can be connected with judicious placement of nanoscale objects. In one embodiment, a template having nanoscale features is used to create electrical connections between different electronic elements and devices. As shown in FIG. 28, a template 2300 with nanoscale openings 2310 and 2320 is shown. The template 2300 is positioned above a first set of wires 2330, 2340. The first set of wires 2330, 2340 is juxtaposed with a first set of electronic elements (not shown). The first set of wires 2330, 2340 are connected to the first set of electronic elements. The nanoscale openings 2310, 2320 are positioned above the first set of wires 2330, 2340. The nanoscale openings 2310, 2320 contain conductive nanoscale objects 2360, 2350, respectively. The conductive nanoscale objects 2350, 2360 make contact with the first set of wires 2330, 2340, respectively. The conductive nanoscale objects 2350, 2360 may protrude out from the top surface of the template 2300, exposing them to conductive contact with wires or other components located on an opposite side of the template from the first set of wires 2330, 2340.

Positioned above the conductive nanoscale objects 2350, 2360 are a second set of wires 2370, 2380. The second set of wires may be juxtaposed with a second set of electronic elements (not shown). In this embodiment, an approach is illustrated for fabricating nanoscale vias. The structure is illustrated having a substrate surface, covered by wires, topped off with a template having nanoparticles within through-vias, then finally topped off with a second set of wires, giving contact between the two sets of wires through the through via's. Depending on the architecture or applications, circuit elements may be present on the bottom level(s), top level(s), both level(s), or none on either level. The first set of electronic elements is positioned on a different level than the second set of electronic elements. The second set of wires 2370, 2380 are in contact with the conductive nanoscale objects 2350, 2360. The conductive nanoscale objects 2350, 2360 provide an electrical contact between the second set of wires 2370, 2380 and the first set of wires 2330, 2340. As a result, the first set of electronic elements will be electrically connected with the second set of electronic elements. Thus, according to embodiments of the invention, templates having nanoscale features and structures can be used to connect electronic elements and devices. The nanoscale features of a template can provide vias through the template. The vias can be used to connect wires or to connect electrical devices.

In another embodiment, the conductive nanoscale objects placed in the template have an insulating oxide on their surface. Thus, this configuration results in each connection becoming a novel device, which works on the principle of Coulomb blockade. Other configurations for contacting materials may be employed using templates, properly placed, and possibly positioned in layers. Such a device passes current only at specific external voltages, and therefore possesses a highly non-linear, step-like current-voltage characteristic. The device can be used as a transistor or threshold switch.

Figure 29:
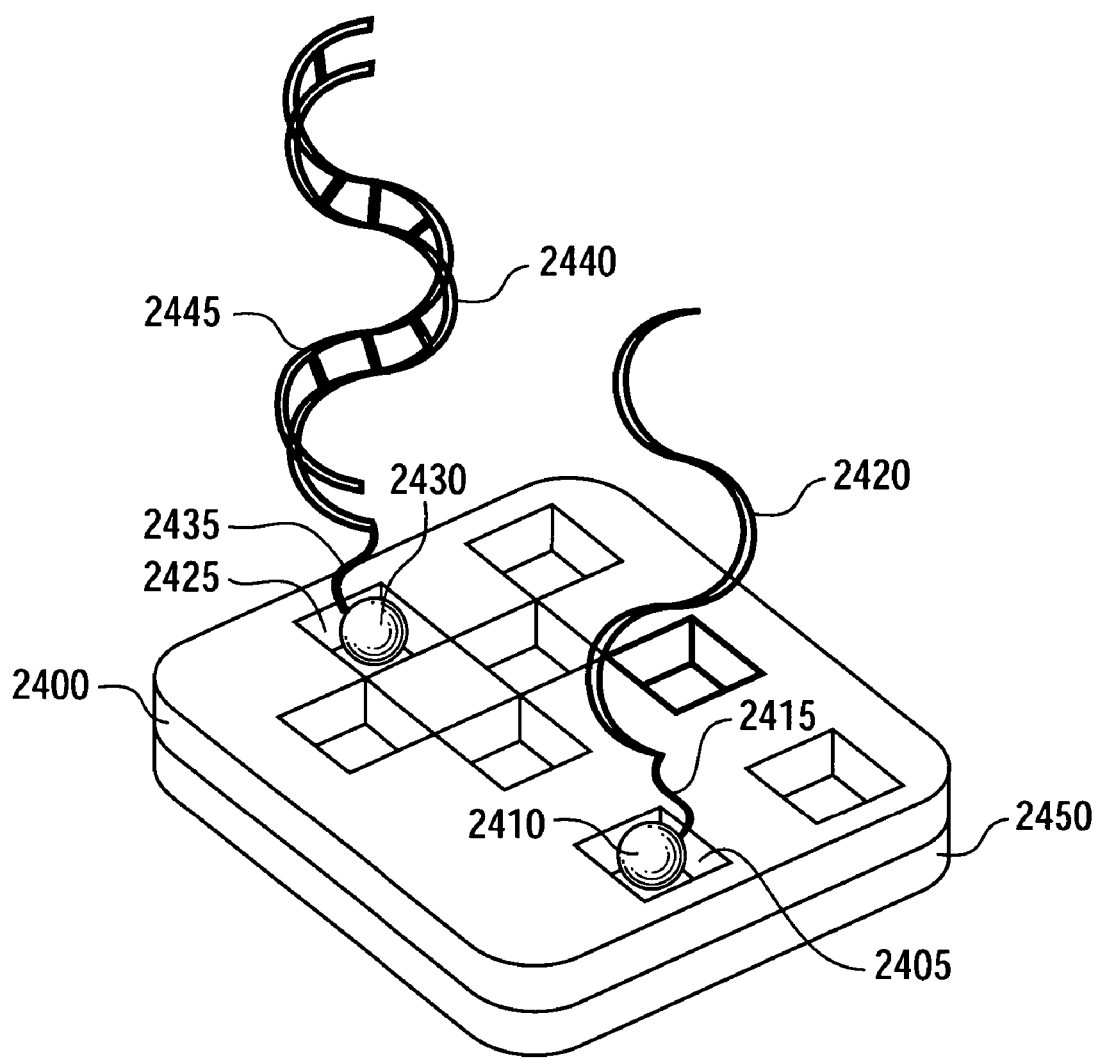
FIG. 29 is an illustration of a template used to construct DNA architectures, in accordance with one embodiment of the invention.

The versatility of the invention is shown in the diversity of its applications. As described above, applications of the invention exist in the electrical arts. Another field where useful applications exist for a template with nanoscale features is biotechnology. FIG. 29 illustrates an embodiment of the invention where a template is provided to construct complex DNA architectures. A template 2400 is used to create a pattern of nanoscale openings on a substrate 2450. The surface of the substrate 2450, upon which the template 2400 is placed, could be composed of a variety of materials. One example of a surface material for the substrate 2450 is resist material The openings on the template 2400 are nanoscale in size. Nanoscale objects 2410, 2430 are positioned in the nanoscale openings 2405, 2425 of the template. Special linker molecules 2415, 2435 are attached to the nanoscale objects 2410 and 2430, respectively. The nanoscale objects 2410, 2430 are tethered with the special linker molecules 2415, 2435 respectively. This embodiment illustrates an application of DNA scaffolding where precise placement of molecules on a substrate is desirable. Another application would be tethering the nanoscale objects with sensor receptors. The special linker molecules 2415, 2435 facilitate the attachment of different structures to the nanoscale objects 2410, 2430. In one embodiment, this attachment is accomplished by bringing the special linker molecules 2415, 2435 into contact with the nanoscale objects 2410 and 2430, respectively. Upon contact, the nanoscale objects 2410, 2430 attach to the special linker molecules 2415, 2435.

The special linker molecule 2415 is shown attached to a DNA oligomer 2420. The attachment is created when the DNA oligomer 2420 and the special linker molecule 2415 contact and attach. With DNA oligomer 2420 attached to special linker molecule 2415 the structure can be built up further.

Special linker molecule 2435 is shown attached to nanoscale object 2430. Further up the figure, DNA oligomer 2440 is attached to special linker molecule 2435. DNA oligomer 2440 is shown with a DNA template (scaffold) 2445 attached. The combination of the DNA oligomer 2440 and the DNA scaffold 2445 forms a dimer. A dimer is a molecule which consists of two similar (but not necessarily identical) subunits. In this embodiment, the precise placement of oligomers on a substrate surface becomes possible. Furthermore, such structures can be used to create more complicated DNA architectures or in biological sensing applications.

Thus linear or non-linear growth of the nanoscale objects can be initiated on a substrate surface. Nanoscale objects can be used for molecular attachment. In one embodiment, the nanoscale objects are comprised of DNA, polynucleic acid, polypeptide, or a layer of organic material. The DNA, polynucleic acid, polypeptides, or layer of chemistry can further be used for chemical sensing applications or as scaffolding material to construct complicated biomolecular architectures.

As discussed above, useful electronic components can be created by judicious choice of semiconductor and conductor materials on a nanoscale. Templates may be configured to apply one-dimensional lines of nanoscale objects or blankets of nanoscale objects. These lines or blankets of particles may be configured to contact other lines or blankets of nanoscale objects by overlapping or otherwise juxtaposing with the other lines or blankets of particles. They may also be configured to contact by employing a bridging contact using an intermediate material. Other configurations for contacting materials may be employed using templates, properly placed, and possibly applied in layers in an iterative process.

According to certain embodiments of the invention, three dimensional components or devices may be created using templates. Different layers of nanoscale objects may be applied to a surface using different templates to place nanoscale objects in locations on a surface with precision. Also, subsequent layers of particles or other material may be layered to create three dimensional components or devices. Using the templates, a designer can have independent control of each layer to create three-dimensional components for use in electrical circuits or in other applications.

For example, two terminal devices can be created from layering two materials of different electrical characteristics. In one embodiment, a via that bridges two different levels in an electrical circuit can be created using a nanoscale object or nanowire positioned in a nanoscale opening in a template. In another embodiment, a two terminal device can be made from a first layer of semiconductor material deposited by a template, followed by a second layer of metallic or conducting material. Tunnel junctions or quantum dots can be created by such material. Such a two terminal device could be a diode, such as a Schottky diode, a metal semiconductor contact structure in which rectification occurs that is influenced by the difference in the charge densities of the materials. One example is an interfacial aluminum/silicon Schottky diode. Another example is an interfacial metal/semiconductor compound such as a silicide. In another embodiment, materials of different magnetic properties can be used to form useful electrical structures. For example, magnetic nanowires of Fe or Co could be created and applied in magnetic storage media.

With the described methods and systems, nanoimprint lithography is being leveraged. Nanoimprint lithography provides the ability to imprint or form nanoscale openings into a photoresist like layer in any desired location. This capability allows one skilled in the art to engineer complex symmetric patterns, non-symmetric patterns, or a combination of both coexisting. The methods and systems described provide an enabling method for patterning substrates with nanoscale features that can be used for subsequent processes. The invention provides the ability to create nanoscale objects on a substrate where the number, size, shape, orientation, pattern, and position of the nanoscale objects are controlled.

The invention has been described with reference to a method for creating nanoscale objects on a substrate where the number, size, shape, pattern, orientation, and position of the objects can be controlled. The scope of the invention extends to a process, a product resulting from a process, a structure, an apparatus, a system, a device or a method. It will be appreciated by those skilled in the art, however, that the invention has broader utility. Other embodiments may be implemented according to the invention without departing from the spirit and scope of the invention, the scope of which is to be construed in accordance with the following claims and their equivalents.

The invention claimed is:

1. A method of fabricating ordered patterns of nanoscale objects on a substrate surface comprising:
   applying a resist layer to a substrate surface;
   stamping an imprint mold having nanoscale teeth onto the resist layer;
   releasing the imprint mold to expose a template having a template surface formed into the imprint resist layer and having nanoscale openings formed therein to receive nanoscale objects; and
   depositing a plurality of discrete nanoscale objects onto the template such that the nanoscale objects are received within said nanoscale openings, said nanoscale objects are selected from the group consisting of nanoparticles, nanowires, nanorods, nanotubes, proteins, and DNA.

2. A method according to claim 1, further comprising selectively removing residual layer material from the substrate surface to expose portions of the substrate surface, and wherein at least some nanoscale objects are in contact with the exposed substrate surface.

3. A method according to claim 1, further comprising:
removing the nanoscale objects that remain outside of the openings with a chemical wash.

4. A method according to claim 1, wherein the nanoscale openings are ordered in a pattern with respect to at least one of the group consisting of size, shape, orientation, pattern, and position.

5. A method according to claim 1, further comprising attaching DNA ogligomers to the nanoscale objects, and wherein the nanoscale objects are proteins.

6. A method according to claim 1, wherein the stamping is performed by a step and flash lithographic method.

7. A method according to claim 1, further comprising forming a first set of wires below the template, and forming a second set of wires above the the template, and wherein the nanoscale objects are conductive and provide electrical connection between the first and second sets of wires.

8. A method of forming a nanoscale object on a substrate surface comprising:
applying a resist layer to a substrate surface;
imprinting a nanoscale opening into the resist layer with a mold;
removing the mold to expose said nanoscale opening in said resist layer, said nanoscale opening sized to receive a nanoscale object therein; and
depositing a nanoscale object onto the resist such that the nanoscale object is receive within said nanoscale opening.

9. A method according to claim 8 wherein said nanoscale object is selected from the group consisting of nanoparticle, nanowires, nanorods, nanotube, proteins, and DNA.

10. A method according to claim 8 wherein a single, discrete nanoscale object is received within a single, discrete nanoscale opening.

11. The method according to claim 8 wherein a plurality of nanoscale objects are received within a plurality of nanoscale openings.

12. The method according to claim 8 wherein said nanoscale object received within said nanoscale opening is in direct contact with said substrate surface.

13. The method of claim 8 further comprising attaching a DNA ogligomer to the nanoscale object.

14. The method according to claim 8 wherein
the nanoscale object is a protein.

* * * * *

UNITED STATES PATENT AND TRADEMARK OFFICE
CERTIFICATE OF CORRECTION

PATENT NO. : 7,597,814 B2  Page 1 of 1
APPLICATION NO. : 10/807873
DATED : October 6, 2009
INVENTOR(S) : James W. Stasiak et al.

It is certified that error appears in the above-identified patent and that said Letters Patent is hereby corrected as shown below:

In column 15, line 12, in Claim 5, delete "ogligomers" and insert -- oligomers --, therefor.

In column 15, line 18, in Claim 7, after "the" delete "the".

In column 16, line 5, in Claim 8, delete "receive" and insert -- received --, therefor.

In column 16, line 7, in Claim 9, delete "A" and insert -- The --, therefor.

In column 16, line 9, in Claim 9, delete "nanotube," and insert -- nanotubes, --, therefor.

In column 16, line 10, in Claim 10, delete "A" and insert -- The --, therefor.

In column 16, line 20, in Claim 13, delete "ogligomer" and insert -- oligomer --, therefor.

Signed and Sealed this

Ninth Day of February, 2010

David J. Kappos
*Director of the United States Patent and Trademark Office*